United States Patent
Koncilja et al.

(10) Patent No.: US 9,447,188 B2
(45) Date of Patent: Sep. 20, 2016

(54) METHOD FOR CONTROLLING THE MAIN COMPLEX N-GLYCAN STRUCTURES AND THE ACIDIC VARIANTS AND VARIABILITY IN BIOPROCESSES PRODUCING RECOMBINANT PROTEINS

(75) Inventors: Matjaž Koncilja, Menges (SI); Vatroslav Spudic, Menges (SI); Saša Stojkovic, Menges (SI); Matjaž Tisu, Menges (SI)

(73) Assignee: LEK PHARMACEUTICALS D.D., Ljubljana (SI)

( * ) Notice: Subject to any disclaimer, the term of this patent is extended or adjusted under 35 U.S.C. 154(b) by 28 days.

(21) Appl. No.: 14/008,933

(22) PCT Filed: Apr. 12, 2012

(86) PCT No.: PCT/EP2012/056672
§ 371 (c)(1),
(2), (4) Date: Dec. 13, 2013

(87) PCT Pub. No.: WO2012/140138
PCT Pub. Date: Oct. 18, 2012

(65) Prior Publication Data
US 2014/0087423 A1    Mar. 27, 2014

(30) Foreign Application Priority Data
Apr. 13, 2011    (EP) .................................... 11162193

(51) Int. Cl.
*C07K 16/28* (2006.01)
*C07K 16/24* (2006.01)
*C07K 16/22* (2006.01)
*C12P 21/02* (2006.01)
*C12N 1/38* (2006.01)

(52) U.S. Cl.
CPC ........... *C07K 16/2887* (2013.01); *C07K 16/22* (2013.01); *C07K 16/241* (2013.01); *C07K 16/2863* (2013.01); *C12N 1/38* (2013.01); *C12P 21/02* (2013.01)

(58) Field of Classification Search
CPC ................................................ C07K 16/2887
See application file for complete search history.

(56) References Cited

U.S. PATENT DOCUMENTS 5,459,031 A * 10/1995 Blumen et al. .................... 435/3
6,338,964 B1    1/2002 Matanguihan et al.

OTHER PUBLICATIONS

Kimura et al (Biotechnol. Prog. 1997; 13:311-317).*
Baselga et al. (Cancer Research.1998; 58:2825-2831).*
Butler, "Optimisation of the cellular metabolism of glycosylation for recombinant proteins produced by mammalian cell systems", *Cytotechnology*, 50:57-76, 2006.
Lipscomb et al., "Effect of production method and gene amplification on the glycosylation pattern of a secreted reporter protein in CHO cells", *Biotechnol Prog.*, 21:40-49, 2005.
PCT International Search Report and Written Opinion issued in International Application No. PCT/EP2012/056672, mailed May 9, 2012.
Schmelzer and Miller et al., "Hyperosmotic stress and elevated $pCO_2$ alter monoclonal antibody charge distribution and monosaccharide content", *Biotechnology Progress*, 18(2):346-53, 2002.
Takuma et al., "Dependence on glucose limitation of the $pCO_2$ influences on CHO cell growth, metabolism and IgG production", *Biotechnology and Bioengineering*, 97(6):1479-1488, 2007.
Trummer et al., "Process parameter shifting: Part II. Biphasic cultivation—a tool for enhancing the volumetric productivity of batch processes using Epo-Fc expressing CHO cells", *Biotechnology and Bioengineering*, 94(6):1045-1052, 2006.
Zanghi et al., "Bicarbonate concentration and osmolality are key determinants in the inhalation of CHO cell polysialylation under elevated $pCO_2$ or pH", *Biotechnology and Bioengineering*, 65(2):182-191, 1999.
Zhu et al., "Effects of elevated $pCO_2$ and osmolality on growth of CHO cells and production of antibody-fusion protein B1: A case study", *Biotechnology Progress*, 21(1):70-77, 2005.

* cited by examiner

*Primary Examiner* — Scott Long
(74) *Attorney, Agent, or Firm* — Parker Highlander PLLC

(57) ABSTRACT

The present invention relates to a method of controlling quality and quantity of posttranslational modification of a recombinantly produced polypeptide/protein (glycoprotein), wherein the posttranslational modification affects the glycosylation profile and/or the acidic variants profile, as manifested in CEX profiles, wherein the polypeptide/protein (glycoprotein) production is in eukaryotic host cells, the method comprising the following steps: a) cultivating the eukaryotic cells in a suitable medium under conditions which allow the expression of the polypeptide/protein, wherein the content of the dissolved $CO_2$ ($pCO_2$) in the medium is at a first value during the initial growth phase of the eukaryotic cells, allowing the eukaryotic cells to grow, and b) increasing or decreasing the content of the dissolved $CO_2$ ($pCO_2$) in the medium during the production phase of the eukaryotic cells to a second value.

18 Claims, 12 Drawing Sheets

Figure 1:
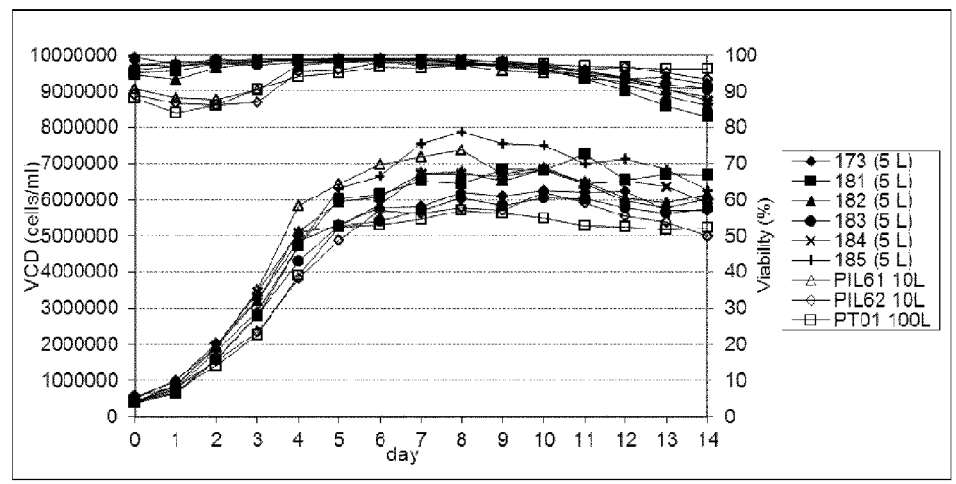

METHOD FOR CONTROLLING THE MAIN COMPLEX N-GLYCAN STRUCTURES AND THE ACIDIC VARIANTS AND VARIABILITY IN BIOPROCESSES PRODUCING RECOMBINANT PROTEINS

This application is a national phase application under 35 U.S.C. §371 of International Application No. PCT/EP2012/056672, filed Apr. 12, 2012, which claims priority to European Application No. 11162193.4, filed Apr. 13, 2011. The entire text of each of the above referenced disclosures is specifically incorporated herein by reference.

The present invention relates to methods for controlling recombinant protein quality attributes and variability in bioprocesses using mammalian cells.

BACKGROUND OF THE INVENTION

It is known that dissolved carbon dioxide alone or in combination with some other factors like osmolality, glucose concentration, or pH can effect cell growth and performance (Zanghi et al., 1999; Takuma et al., 2007). All publications describing methods utilising dissolved carbon dioxide to regulate cell growth report on a $CO_2$ partial pressure ($pCO_2$) that is kept constant throughout the whole bioprocess.

Zanghi et al. (1999) have further focused on the effect $pCO_2$ has on glycosylation of recombinant proteins, and concluded that under elevated $pCO_2$ the intracellular pH can be affected which leads to decreased activity of pH-sensitive sialyltransferases and consequently to decreased polysialylation of recombinant proteins.

Takuma et al. (2007) have found that the sugar mapping profile was significantly affected by glucose concentrations, where at higher glucose conditions the relative bG0 peak area was higher, while on the other hand they did not find a consistent dependence on $pCO_2$.

Only two references were found to mention a strategy for influencing the degree of glycosylation and the glycosylation profile in the product by dissolved $CO_2$ in cell culture bioprocesses. Whereas one demonstrates a negative correlation between $pCO_2$ and product polysialylation (Zanghi et al., 1999), the other (Takuma et al. 2007) concludes that no consistent dependence of glycan structures bG0 and bG1 on $pCO_2$ can be found.

Protein glycosylation typically leads to a diversity of proteins distinguished by their glycosylation profiles (patterns), which diversity is due to multiple factors. The question of native versus foreign glycosylation in humans is a contentious subject: It is not totally clear which state is the native glycosylation state, since it varies frequently between different and even within one species. This is especially true in IgG, the backbone molecule of most therapeutic monoclonal antibodies, but likewise applies to many other (types of) polypeptides and proteins.

Even with knowledge of the glycosylation profile of a particular human glycoprotein, matching those attributes of the recombinant protein produced in a bioprocess is not trivial. The choice of the host cell as the expression system has a primary role towards the resulting glycosylation profile of the respective polypeptide.

The three most common cell culture production modes are batch, fed-batch, and perfusion. The production method can have a pronounced effect on the resulting glycosylation profile. The glycosylation profile of the reporter protein-secreted alkaline phosphatase (SEAP) produced by a CHO DG44 cell line was compared between different process parameters: unamplified versus MTX-amplified cell lines, batch mode versus repeated fed-batch mode versus semi-continuous perfusion mode (Lipscomb et al., 2005). The glycosylation profile of the MTX-amplified cell line exhibited less mannosylated polypeptides, as well as less overall sialylation, although these differences were less than 10% of the total profile (that is, more than 90% of the sugar moieties attached to the polypeptides were the same and at the same position, regardless which process parameters had been selected). Overall sialylation was increased in the perfusion mode cultures compared to fed-batch mode, the slower growing cells in perfusion mode facilitated a more fully glycosylated polypeptide compared to the fed-batch mode where cells grew faster.

Researchers investigated the effect of various process parameters on the resulting EPO-Fc glycoprotein (EPO=erythropoietin) expressed by CHO cells in a bioreactor (Trummer et al., 2006). It was found that the sialic acid ratio (i.e., molar ratio NANA/glycoprotein; NANA=N-acetylneuraminic acid) in the glycoprotein had a maximum of about 13% when cultivated at around pH 7.0, which ratio decreased if the pH deviated therefrom. The optimal level of dissolved oxygen (DO) for the maximum ratio was accomplished by 50% of air saturation (the relationship pH/DO is that the DO level may indirectly interfere with pH, since pH is controlled by $CO_2$/base, and $CO_2$ addition can cause stripping of $O_2$ from the vessel; e.g., high DO levels and low pH set-points can cause big oscillations in pH and $pO_2$).

Similarly, the sialic acid ratio decreased from 13 to only 8% when the culture temperature was brought down from 37° C. to 30° C. This process mapping is a fine example of range-finding efforts that are pivotal towards process understanding and effective process control and its impact on protein glycosylation. DO levels were monitored continuously throughout the process of culturing mammalian cells and have been shown to affect the glycosylation profiles. Hypoxia in bioreactor cultures has shown ambiguous effects on protein glycosylation. For example, only minor changes were observed for tPA glycosylation, but significant sialylation changes were observed for FSH, although both proteins were produced by CHO cells. An IgG1 glycoprotein, expressed by a murine hybridoma at DO levels of 100, 50, and 10%, had a degree of galactosylation decreasing with the DO level.

Ammonium ions are a cellular waste product, generally toxic to cells, and accumulate in cell culture media principally as a result of glutamine and asparagine metabolism Ammonium chloride causes an increase in intracellular pH. Since terminal glycosylation occurs in the acidic distal regions of the Golgi complex, an increased level of ammonium chloride in the medium may, via an intracellular pH increase, correlate with a decrease in terminal sialylation.

The pH of the medium in the bioreactor has also been found to affect glycosylation profiles. The pH of a hybridoma culture has been shown to affect the resulting galactosylation and sialylation of the antibody. The highest levels of a-galacto- and mono-galacto-complex-type N-glycans were measured at pH ranging from 7.2 to 6.9, and the highest di-galacto-complex-type N-glycans were measured at pH 7.4, both in HEPES-buffered cultures. The latter condition also facilitated the highest NANA/NGNA (NGNA=N-glycolylneuraminic acid) ratio, compared to any of the pH experiments.

The proportion of acidic isoforms of EPO increased with decreasing pH of the cell culture, with optimal ranges of 6.8-7.2 favouring sialylation. Interestingly, even though higher pH and higher buffered conditions facilitated higher NANA contents, the opposite was found with polysialic acid attached to neural cell adhesion molecules (NCAM) expressed on recombinant CHO cell surfaces.

Reducing the temperature can increase overall polypeptide production by prolonging cell viability which should basically improve glycosylation (generally, improved glycosylation means a glycosylation profile coming closest to the profile of the originator protein/antibody; here, improved glycosylation means a higher degree of glycosylation). Cell viability is critical because extracellular glycosidases can accumulate in the medium and step-wise remove monosaccharides from the glycoprotein. Temperature shifts in a bioreactor can increase the product titre while maintaining glycoform quality (i.e., distribution of the glycoforms, in %). In contrast, EPO-Fc had a decrease in sialylation by 20% and 40%, when reducing the temperature to 33° C. and 30° C., respectively (Trummer et al., 2006). In this specific case, a reduced temperature of 30° C. showed a correlation between increased specific productivity and decreased levels of sialylation. It is still unknown, however, whether higher productivity correlates with the expression rate, thereby reducing the intracellular processing time for glycosylation and causing an increase in less sialylated protein populations. High cell viability (less sialidase activity) in conjunction with high cell productivity (shorter residence time) may diminish the overall effect on sialylation, i.e., cause sialylation to decrease.

Finally, shear stress in a bioreactor culture has been reported to be an important parameter to determine the resulting glycosylation profile. By manipulating agitation speeds and the resulting shear stress, it was found that maximum levels of damaging shear were required to minimise the extent of carbohydrate attachment to Asn184 in tPA, which was attributed to a decreased residence time of tPA in the ER. This can be an important consideration during scale-up or transfer of an existing process to a different facility. Monitoring the effects of shear differences on protein glycosylation during the transition between production modes (e.g., from perfusion to fedbatch) is also important for ensuring product comparability.

The above process parameters and further factors potentially having an impact on the glycosylation profile of a given polypeptide are a challenge for biopharmaceutical companies, where the change of the cell line, of process parameters, and/or of manufacturing site(s) may require extensive comparative studies to prove that the molecule remains the same. This was highlighted in the case of Genzyme's recombinant enzyme Myozyme. Genzyme was unable to demonstrate by FDA standards that Myozyme had the same carbohydrate structure when transferring the manufacturing process from the 160- to the 2000-liter bioreactor scale, underlining how critical it is to understand what affects the glycosylation profile.

Thus, in order to achieve comparability (within the meaning of similarity or even identity) between polypeptide products produced by different companies and/or via different methods (e.g., between a product of an originator and the corresponding product, i.e., the biosimilar, of another company), a method for controlling the glycosylation profile, posttranslational modifications manifested in CEX (cationic exchange chromatography) profiles, and variability between bioprocesses (variability also including growth profiles, metabolism, i.e., substrate consumption and metabolite production, product formation) would be extremely straightforward and desired.

In particular, the principal object underlying the present invention is to provide a method that allows to control the glycosylation profile and acidic variants in products produced in bioreactors (e.g., recombinant antibodies, cytokines, enzymes, hormones, growth factors) by only one parameter that is optionally easily set and regulated. Accordingly, such method would contribute to and enrich the art quite significantly.

SUMMARY OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an", and "the" include singular and/or plural referents unless the context clearly dictates otherwise. It is moreover to be understood that, in case parameter ranges are given which are delimited by numeric values, the ranges are deemed to include these limitation values.

Motivated by the above downsides in the art and the enormous improvement in case of success, and starting from that demand, the present inventors developed, established, and now provide the following method according to the invention: A method to control (i) the glycosylation profile (also termed glycosylation pattern or N-glycan profile; while glycans are sometimes defined as oligo-/polysaccharides, glycans in the present context more specifically refer to an oligosaccharide N-linked to a polypeptide, wherein linkage of the oligosaccharide to the polypeptide regularly occurs via the nitrogen of the side chain of Asn or Arg), (ii) the amount/percentage of acidic variants (acidic variants profile), (iii) posttranslational modifications, as manifested in CEX profiles, and (iv) variability in polypeptide products (e.g., recombinant antibodies) obtained by means of different bioprocesses simply by regulating nothing more than $pCO_2$.

Actually, the present invention relates to a novel method, wherein eukaryotic, in particular, mammalian cells are cultivated in a medium to allow for the expression of a desired polypeptide. The content of dissolved carbon dioxide ($pCO_2$) in the medium during the first (initial) growth phase (usually days 0 to 3) of the cells is maintained at a first value, allowing the eukaryotic cells to grow (also termed the first $pCO_2$ set-point or the first set-point), preferably at ≤10%. Later, in the production phase (e.g., starting at day 4) of the cells, the content of dissolved carbon dioxide ($pCO_2$) in the medium is increased or decreased to a second value (also termed the second $pCO_2$ set-point or the second set-point), that is preferably in the range of >10 to 40%, if the second value is increased (for more details in regard of the second set-point see further below).

Thus, the method of the invention is defined as a method of controlling quality and quantity of posttranslational modification of a recombinantly produced polypeptide, wherein the posttranslational modification affects the glycosylation profile and/or the acidic variants profile, the method comprising the following steps:

a) cultivating eukaryotic cells in a suitable medium under conditions which allow the expression of the polypeptide, wherein the content of the dissolved $CO_2$ ($pCO_2$) in the medium is maintained at a first value, allowing the eukaryotic cells to grow during the initial growth phase, and b) increasing or decreasing the content of the dissolved $CO_2$ ($pCO_2$) in the medium during the production phase of the eukaryotic cells to a second value.

The step of decreasing $pCO_2$ in the medium is preferably performed by allowing the $CO_2$ to escape from the medium (by not replacing it by new $CO_2$). However, any other means of stripping $CO_2$ out as known to the skilled person is likewise appropriate.

Implementation of the method according to the invention improves product quality in regard of glycosylation and charged variants profiles of the polypeptides produced and lowers variability between polypeptides obtained by distinct bioprocesses, at distinct places, and under distinct conditions. Actually, although the two publications discussed above (Zanghi et al., 1999; Takuma et al., 2007) discuss $pCO_2$ in the context of protein glycosylation, none mentions or suggests to set and regulate $pCO_2$ during the bioprocess at two or more values, thereby directly affecting the N-glycan structure and acidic variants of the product (recombinant polypeptide).

According to a first preferred embodiment, the method of the present invention is a method, wherein the glycosylation profiles are selected from (i) bG0 structures such as bG0 (—N), bG0(—F), and bG0, and from (ii) bG1 structures such as bG1(—N), bG1(1-6), and bG1(1-3).

According to a second preferred embodiment, the method of the present invention is a method, wherein the second set-point is higher than the first set-point, which brings about that the amount of bG0 structures is increased and the amount of bG1 structures is decreased, relative to the amounts obtained by a method with no $pCO_2$ regulation. Alternatively but not regularly desired, the second set-point is lower than the first set-point, which brings about that the amount of bG0 structures is decreased and the amount of bG1 structures is increased, relative to the amounts obtained by a method with no $pCO_2$ regulation. In other words, the present invention allows for both (i) an up-regulation of the bG0 level (and a down-regulation of the bG1 level) by increasing the second $pCO_2$ set-point relative to the first set-point and (ii) a down-regulation of the bG0 level (and an up-regulation of the bG1 level) by lowering the second $pCO_2$ set-point relative to the first set-point. Thus, control of the bG0/bG1 levels works in both directions which is most desirable and important, because sometimes you want to increase and sometimes to decrease bG0, depending on the bG0 level of the, e.g., biosimilar polypeptide relative to the originator polypeptide.

According to a third preferred embodiment, the method of the present invention is a method, wherein the acidic variants are selected from deamidated, isomerised, glycated, and sialylated variants of the recombinantly produced polypeptide.

According to a fourth preferred embodiment, the method of the present invention is a method, wherein the acidic variants are defined by a reduced amount, relative to the amount obtained by a method with no $pCO_2$ regulation, of acidic variants in the recombinantly produced polypeptide.

According to a fifth preferred embodiment, the method of the present invention is a method, wherein the first $pCO_2$ value is set at ≤10% and the second $pCO_2$ value is set at >10%.

According to a sixth preferred embodiment, the method of the present invention is a method, wherein the first $pCO_2$ set-point is in the range of 2% to 8%, preferably in the range of 3.5% to 6.5%, or 4.5% to 5.5%, and the second $pCO_2$ set-point is in the range of 11% to 40%, preferably in the range of 12% to 35%, 15% to 25%, or 18.5% to 22.5%.

According to a seventh preferred embodiment, the method of the present invention is a method, wherein the cell is an insect or mammalian cell.

According to an eighth preferred embodiment, the method of the present invention is a method, wherein the mammalian cell is a CHO cell or a hybridoma.

According to a ninth preferred embodiment, the method of the present invention is a method, wherein the glycosylated polypeptide is an antibody, or a fragment or derivative thereof.

According to a tenth preferred embodiment, the method of the present invention is a method, wherein said antibody, or fragment or derivative thereof, is selected from:
   a) a hybridoma-derived antibody, fragment, or derivative thereof,
   b) a chimerised antibody, fragment, or derivative thereof,
   c) a humanised antibody, fragment, or derivative thereof, and/or
   d) a human antibody, fragment, or derivative thereof.

According to an eleventh preferred embodiment, the method of the present invention is a method, wherein said antibody, fragment, or derivative thereof, is an IgG, an IgG fragment, or an IgG derivative.

According to a further preferred embodiment, the method of the present invention is a method, wherein said antibody, fragment, or derivative thereof is an antibody that recognises any one or a combination of two or more proteins including, but not limited to, any of the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1a, IL-1, IL-2, IL-3, IL-7, IL-4, IL-5, IL-8, IL-10, IL-2 receptor, IL-4 receptor, IL-6 receptor, IL-13 receptor, IL-18 receptor subunits, PDGF-β, and analogues thereof, PLGF, VEGF, TGF, TGF-β2, TGF-p1, EGF receptor, PLGF receptor, VEGF receptor, hepatocyte growth factor, osteoprotegerin ligand, interferon gamma, B lymphocyte stimulator, C5 complement, IgE, tumour antigen CA125, tumour antigen MUC1, PEM antigen, ErbB2/HER-2, tumour-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumour, integrin alpha 4 beta 7, the integrin VLA-4, B2 integrins, TRAIL receptors 1, 2, 3, and 4, RANK, a RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, MHC I, carcinoembryonic antigen (CEA), alpha-fetoprotein (AFP), tumour necrosis factor (TNF), Fc-y-1 receptor, HLA-DR 10 beta, HLA-DR antigen, L-selectin, and IFN-γ.

According to still a further preferred embodiment, the method of the present invention is a method, wherein the $pCO_2$ in the medium according to the second $pCO_2$ set-point is achieved by stepwise or gradually increasing/decreasing/stopping the addition of $CO_2$ to the medium.

According to still another preferred embodiment, the method of the present invention is a method, wherein the content of dissolved $CO_2$ ($pCO_2$) in the medium is directly regulated by means of a control system with a $pCO_2$-controller equipped with a mass flow controller.

According to still another preferred embodiment, the method of the present invention is a method, wherein the content of dissolved $CO_2$ ($pCO_2$) in the medium is indirectly regulated by regulating the pH.

Direct regulation means regulation of $pCO_2$ by using a $CO_2$ controller (a $pCO_2$ controller measures $pCO_2$ in the medium and adds $CO_2$ to the medium as needed, so that a pre-determined $pCO_2$ value is maintained). The $pCO_2$ controller is optional during the initial growth phase but mandatory subsequently (during the production phase, e.g., starting at day 4). In fact, since the first $pCO_2$ set-point is ≤10%, it may even be 0% (theoretically, at the very least). Thus, in such case (0%) a $pCO_2$ controller would not be needed at all during the initial growth phase, so there is no need to use it. However, a $pCO_2$ controller is definitively needed during the production phase, depending on the demand to (significantly or insignificantly) increase/decrease the bG0 level.

In the indirect regulation, a pH controller (a pH controller measures the pH of the medium and adds $CO_2$, but no acid, to the medium as needed, i.e., in case of an alkaline pH, so that a pre-determined pH is maintained) is used exclusively. That is, the $pCO_2$ controller is switched off during the entire cultivation process. The pH controller is set to an acidic pH (which is regularly reached in the medium due to the metabolites generated by the cells during the cultivation process) in the production phase. Once the cells start to consume the acidic metabolites (e.g. lactate), in case of deactivated pH controller, the medium pH would increase again. The pH controller, if activated and loaded with a set-point defined at the same/lower pH compared to the pH at the time before start of acidic metabolites consumption, will maintain the pH at an acidic value by adding $CO_2$ to the medium. The addition of $CO_2$ entails an increase of the $pCO_2$, relative to the $pCO_2$ in the initial growth phase.

In conclusion, both the direct and indirect $pCO_2$ regulation are based on the same principle, i.e., the addition/stripping out of $CO_2$ into/from the medium during the production phase. This reflects the gist of the invention which is the (antipodal) effect of $pCO_2$ on the bG0 and bG1 glycosylation.

Since there are no new substrates or bioprocess metabolites introduced into the novel bioprocess according to the invention (the inventive method is restricted to the selective effect of $pCO_2$ regulation on glycosylation and the CEX profile of proteins such as antibodies (e.g., IgG)), the method of the invention can be used even in late phases of developing therapeutic biopharmaceuticals and biosimilars, and it may likewise be utilised in an attempt to optimise a bioprocess, to scale up, to transfer the bioprocess plant from one place to another, or to assist in troubleshooting activities. Additionally, the inventive method significantly lowers the risk of batch failure by lowering the variability of product quality between various bioprocesses.

The method according to the present invention, i.e., to regulate the content of dissolved carbon dioxide throughout the process of generating the desired polypeptide, can be applied directly (by using a $CO_2$ controller) or indirectly (by, e.g., regulating the pH, which is down-regulated by additional $CO_2$). In the former direct method, the $pCO_2$ may be set at two or more values, or it may be set to change gradually. In both the set values and gradual change alternatives the initial (growth phase) values are distinct (lower/higher) than are the values later in the production phase.

The alternative way of indirect regulation is exemplified as follows:

The initial pH set-point is lower than, but close to, the pH of the medium, thereby preventing the addition of large amounts of $CO_2$ into the cell culture. The pH controller is turned on only transiently (or turned off from the beginning). Subsequently, the pH controller is turned off (unless it was turned off from the beginning). In other words, now that the pH controller is switched off, the pH of the cell culture decreases by the cells' activity to metabolise/release substances like lactate and $CO_2$ into the culture medium. Following the pH decrease caused by the metabolites, the pH controller is activated (again) and the second pH set-point set (and optionally maintained throughout the rest of the cultivation process) to a pH reached after the natural pH shift or below. This course of action causes the addition of $CO_2$ in an attempt to regulate the pH of the cell culture. When subsequently lactate is consumed (which is quite a common phenomenon in bioprocesses), the consequent increase in the pH value of the cell culture may be prevented by, as required under the circumstances, keeping the pH controller activated.

DEFINITIONS

As used herein, the terms "concentration of dissolved $CO_2$", "dissolved carbon dioxide content", and "partial $CO_2$ pressure ($pCO_2$)" are synonymous, and define the amount of $CO_2$ dissolved or the concentration of dissolved $CO_2$ in the medium (all given in % (v/v)).

The terms "polypeptide" and "protein" are used interchangeably herein. In other words, whenever one of the terms is utilised, it is not restricted to only the strict meaning of that term but also includes the form strictly characterised only by the other. To give an example, an expression construct harbouring the coding sequence of one polypeptide chain of a protein composed of two or more (distinct) polypeptide chains produces, under the appropriate conditions, the respective polypeptide, but it does not produce the respective (multimeric) protein, strictly speaking. Or vice versa, an expression construct harbouring the coding sequence of a protein composed of only a single polypeptide chain produces, under the appropriate conditions, the respective protein, but it does not produce a polypeptide, strictly speaking. In the present application, "polypeptide" and "protein" are used interchangeably, as mentioned before, and the skilled person knows when to "translate" "polypeptide" into "protein", or vice versa.

As used herein, the term "monoclonal antibody (mAb)", shall refer to an antibody composition having a homogenous antibody population, i.e., a homogeneous population consisting of a whole immunoglobulin, or a fragment or derivative thereof. Particularly preferred, such antibody is selected from the group consisting of IgG, IgD, IgE, IgA, and/or IgM, or a fragment or derivative thereof.

As used herein, the term "fragment" shall refer to fragments of such antibody retaining, in some cases, target binding capacities, e.g.,
 a CDR (complementarity determining region)
 a hypervariable region,
 a variable domain (Fv)
 an IgG heavy chain (consisting of VH, CH1, hinge, CH2 and CH3 regions)
 an IgG light chain (consisting of VL and CL regions), and/or
 a Fab and/or F(ab)$_2$.

As used herein, the term "derivative" shall refer to protein constructs being structurally different from, but still having some structural relationship to, the common antibody concept, e.g., scFv, Fab, and/or F(ab)$_2$, as well as bi-, tri-, or higher specific antibody constructs. All these items are explained below.

Other antibody derivatives known to the skilled person are Diabodies, Camelid Antibodies, Domain Antibodies, bivalent homodimers with two chains consisting of scFvs, IgAs (two IgG structures joined by a J chain and a secretory component), shark antibodies, antibodies consisting of new world primate framework plus non-new world primate CDR, dimerised constructs comprising CH3+VL+VH, and antibody conjugates (e.g., antibody or fragments or derivatives linked to a toxin, a cytokine, a radioisotope, or a label).

Methods for the production and/or selection of chimeric, humanised, and/or human mAbs are known in the art. For example, U.S. Pat. No. 6,331,415 by Genentech describes the production of chimeric antibodies, while U.S. Pat. No. 6,548,640 by Medical Research Council describes CDR grafting techniques and U.S. Pat. No. 5,859,205 by Celltech describes the production of humanised antibodies. In vitro antibody libraries are, among others, disclosed in U.S. Pat. No. 6,300,064 by MorphoSys and in U.S. Pat. No. 6,248,516 by MRC/Scripps/Stratagene. Phage display techniques are for example disclosed in U.S. Pat. No. 5,223,409 by Dyax. Transgenic mammal platforms are for example described in US 200302048621 by TaconicArtemis.

IgG, scFv, Fab and/or F(ab)$_2$ are antibody formats well known to the skilled person. Related enabling techniques are available from the respective textbooks.

As used herein, the term "Fab" relates to an IgG fragment comprising the antigen binding region, said fragment being composed of one constant and one variable domain from each heavy and light chain of the antibody.

As used herein, the term "F(ab)$_2$" relates to an IgG fragment consisting of two Fab fragments connected to one another by disulfide bonds.

As used herein, the term "scFv" relates to a single-chain variable fragment being a fusion of the variable regions of the heavy and light chains of immunoglobulins, linked together without or with a short linker, usually consisting of serine (S) and/or glycine (G) residues. This chimeric molecule retains the specificity of the original immunoglobulin, despite removal of the constant regions and the optional introduction of a linker peptide.

Modified antibody formats are for example bi- or trispecific antibody constructs, antibody-based fusion proteins, immunoconjugates, and the like.

As used herein, the terms "glycosylation profile" and "linear- or non-complex-type N-glycan profile" stand for the qualitative and quantitative description of the unbranched (linear) oligosaccharides linked to a protein via the nitrogen of the Asn and/or Arg side chains. In contrast thereto, complex-type N-glycans are bi-, tri-, and tetra-antennary, that is, branched N-glycans are linked to Asn and/or Arg side chains (one glycan is linked to Asn/Arg and then it is further branched: in case of tri-antennary into 3 glycan branches, and in case of bi-antennary into 2 glycan branches (see Table 3, all glycans are bi-antennary)). Their glycosylation profiles are thus termed "complex-type N-glycan profiles".

As used herein, the terms "the acidic variants profile", "the acidic variants pattern", and the like are synonymous and define the quantitative and qualitative distribution of amino acid residues posttranslationally modified (e.g., by deamidation, isomerisation, glycation, sialylation, etc.), as determined by CEX profiles.

The terms of the various non-galactosylated and galactosylated glycoforms, including bG0, bG1(1-3), and bG1(1-6), are as further described and explained in Table 3.

Figure 2:
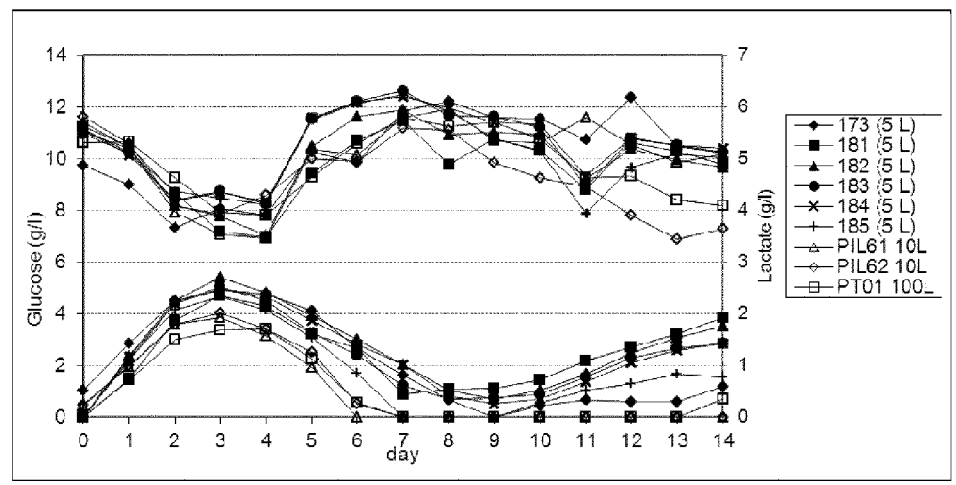
Figure 3:
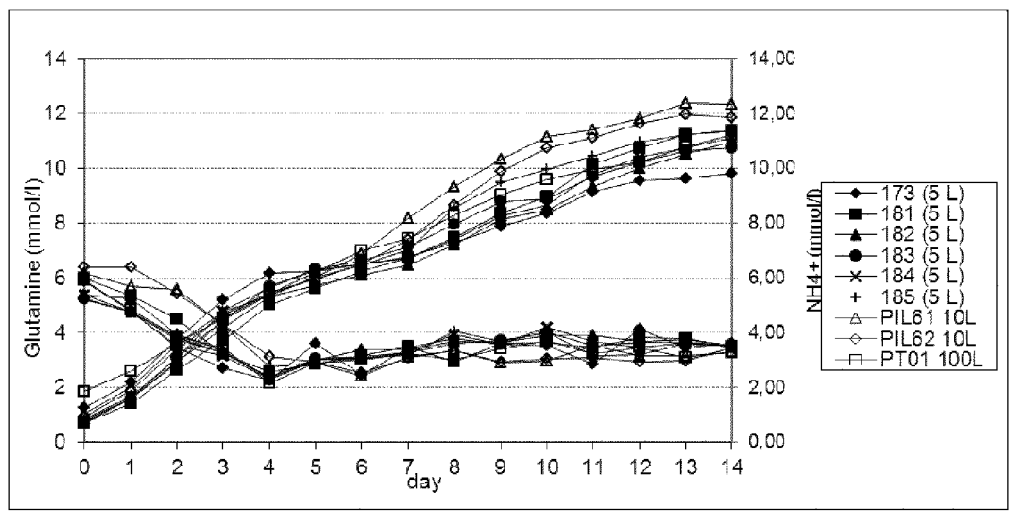
Figure 4:
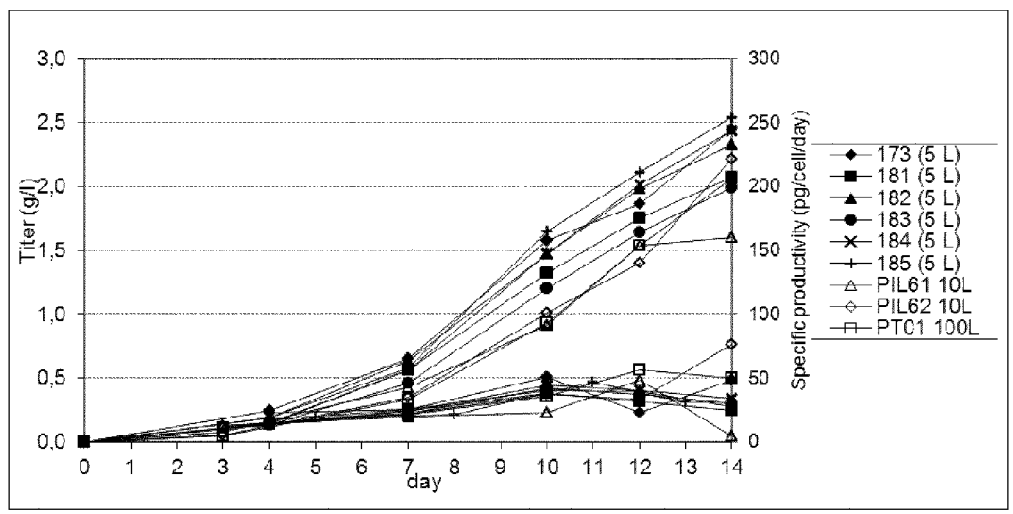
Figure 5:
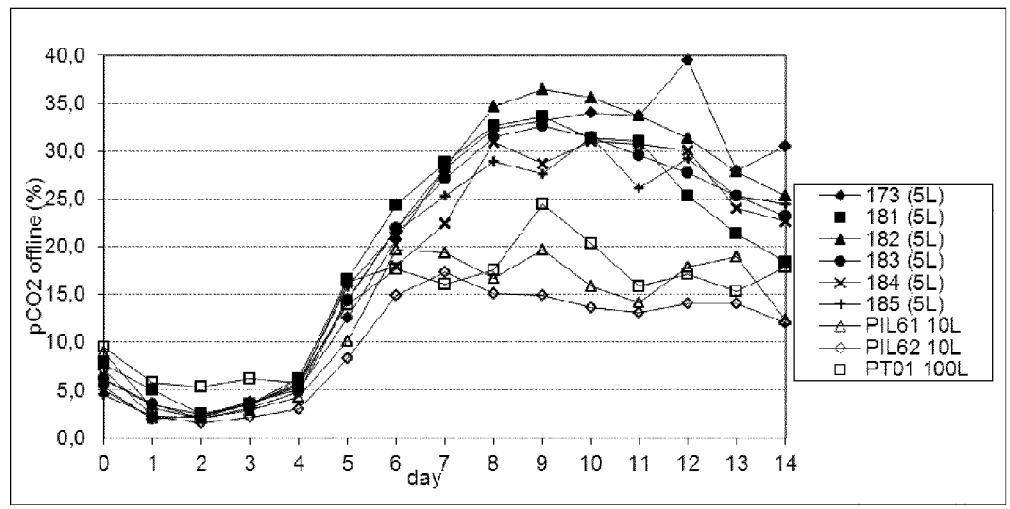
Figure 6:
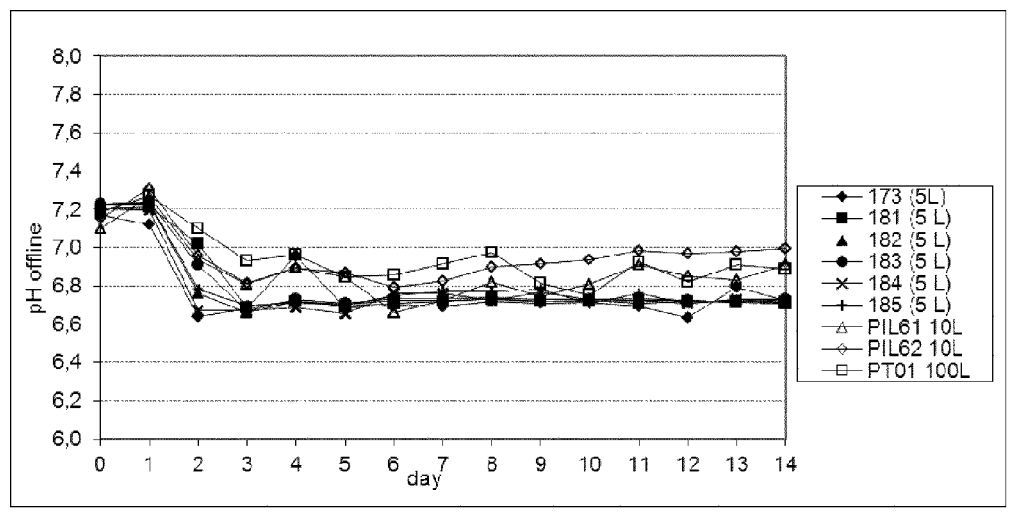
Figure 7:
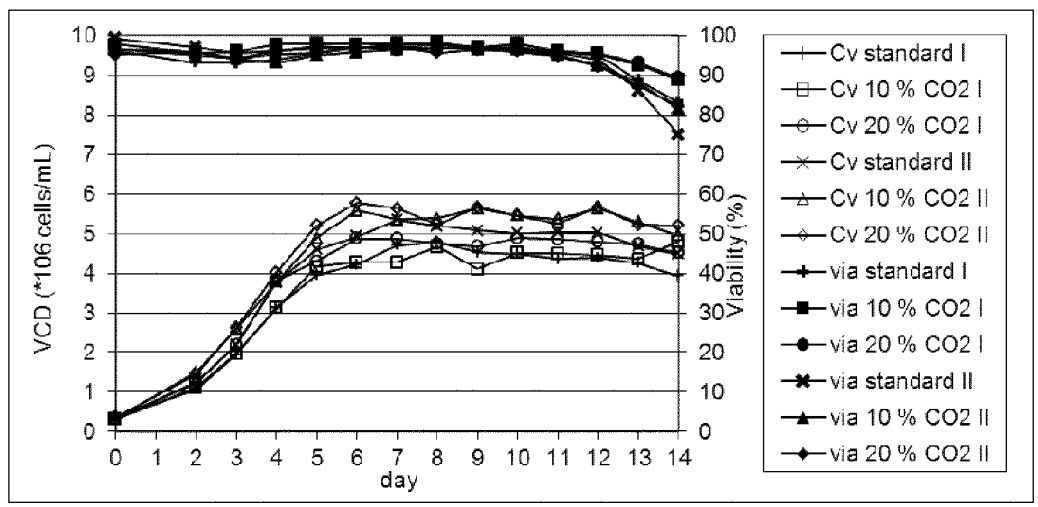
Figure 8:
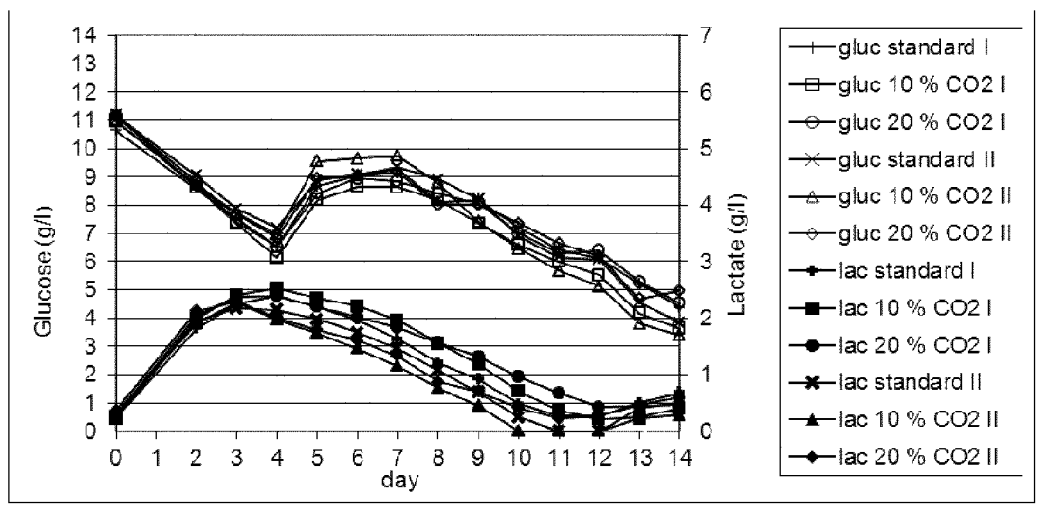
Figure 9:
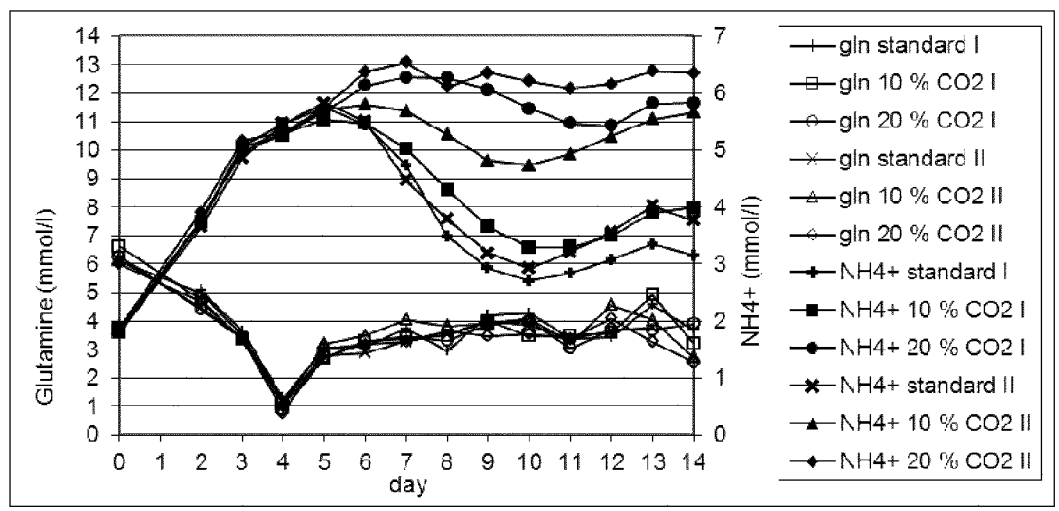
Figure 10:
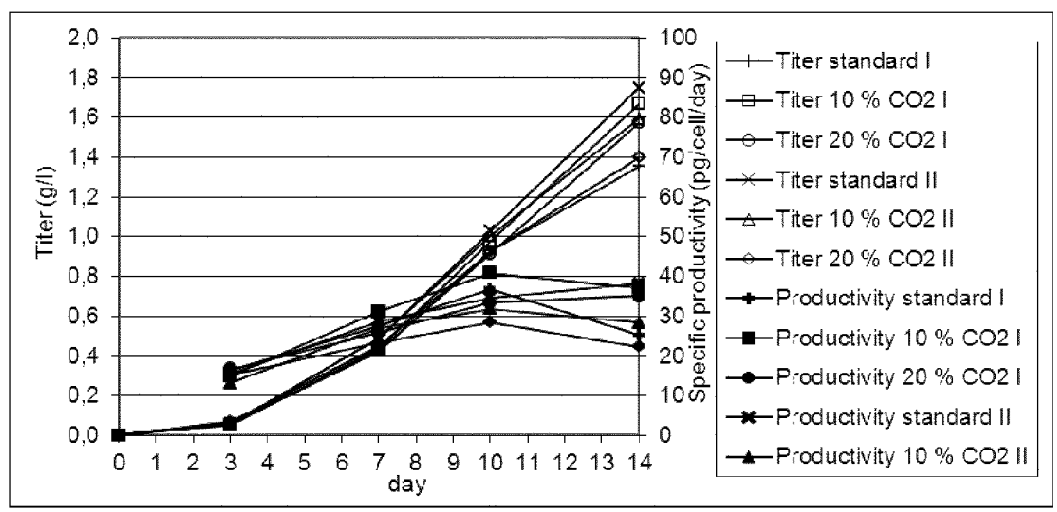
Figure 11:
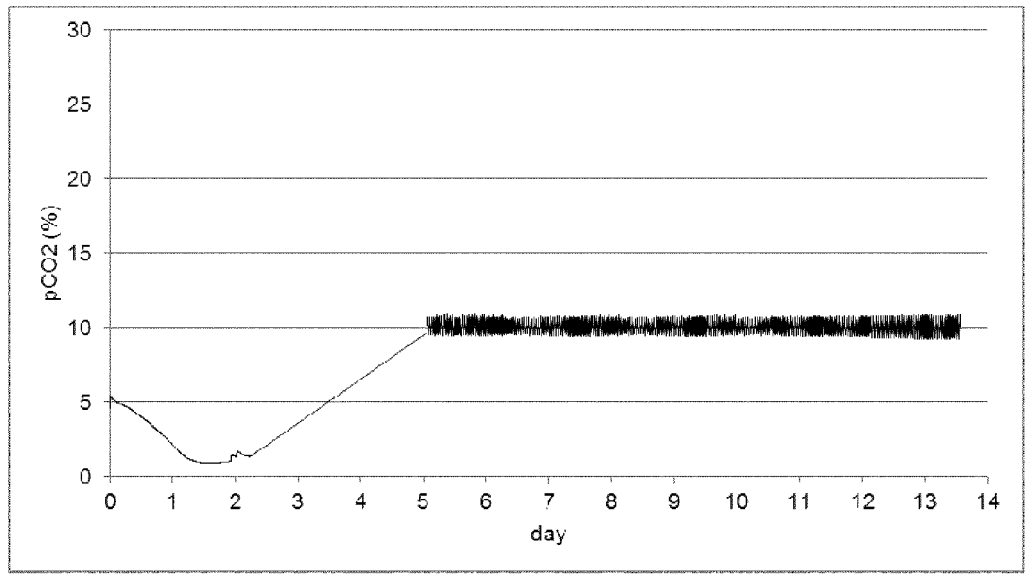
Figure 12:
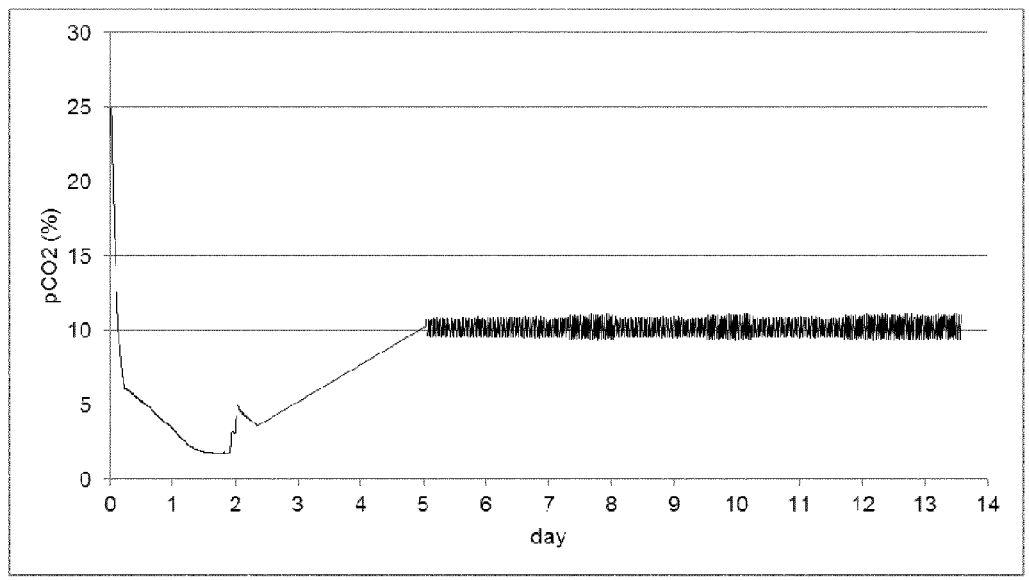
Figure 13:
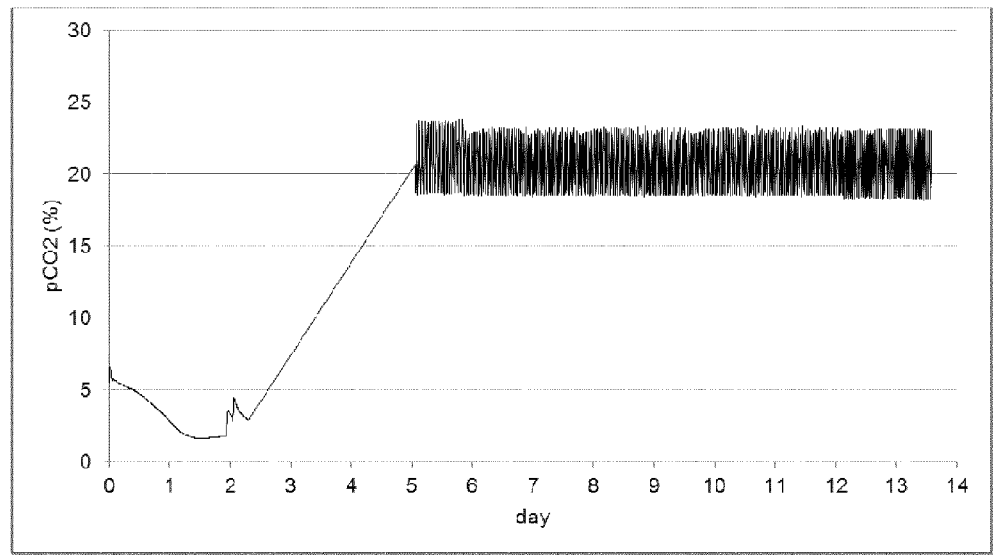
Figure 14:
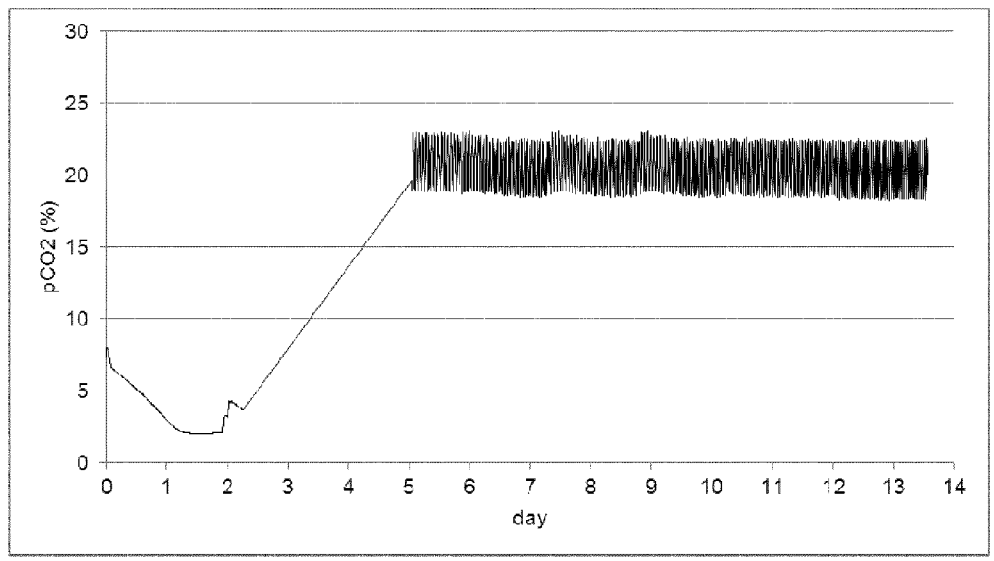
Figure 15:
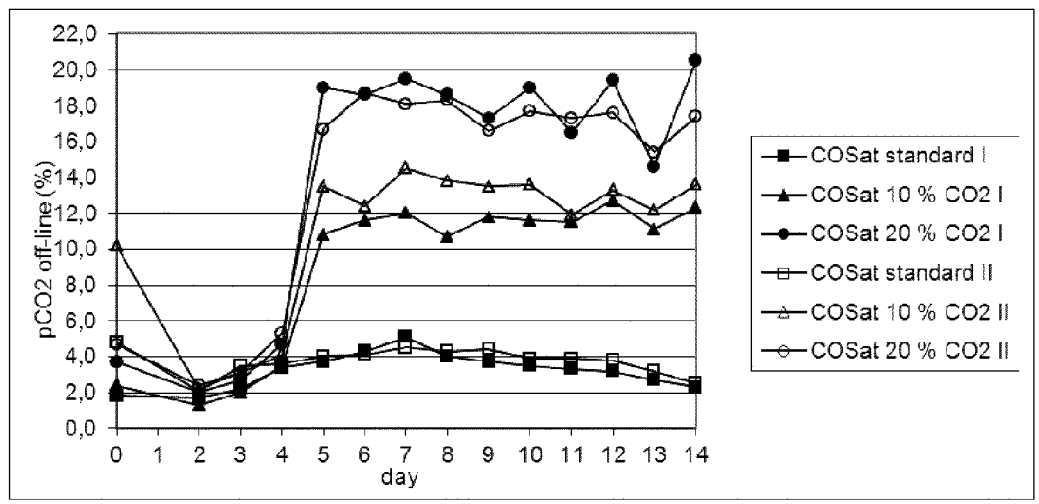
Figure 16:
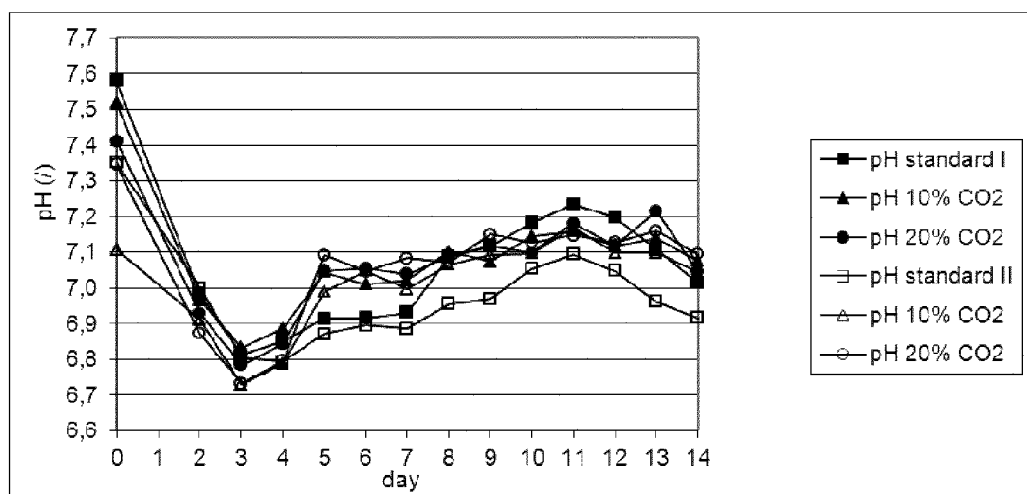
Figure 17:
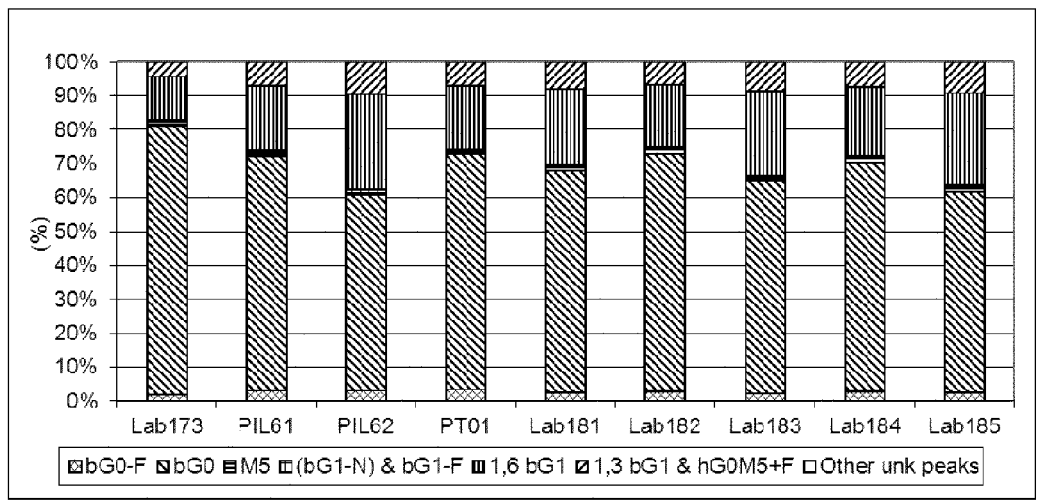
Figure 18:
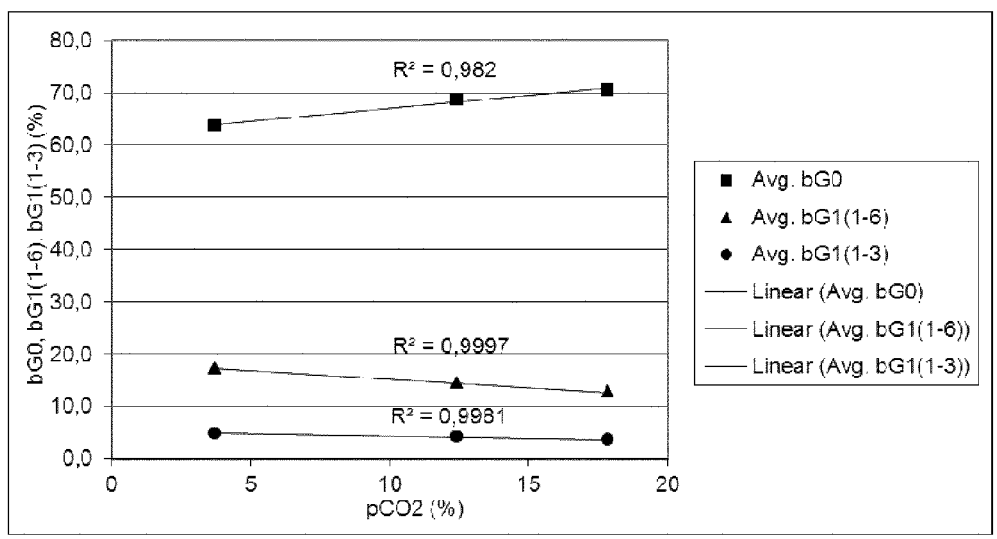
Figure 19:
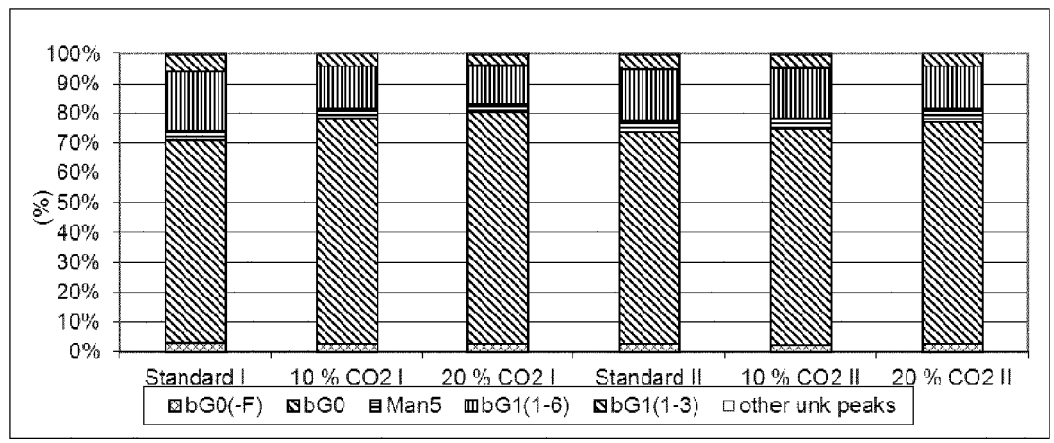
Figure 20:
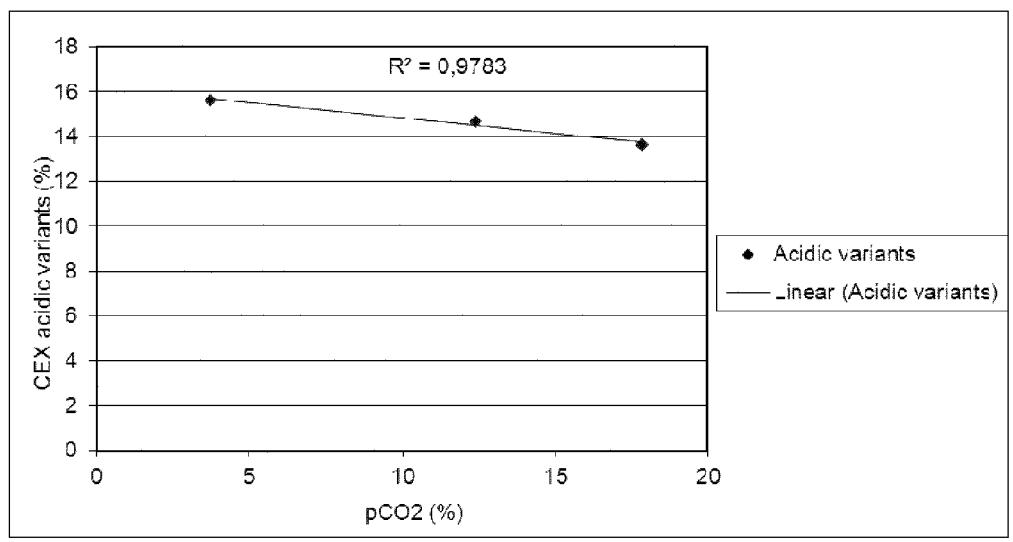
Figure 21:
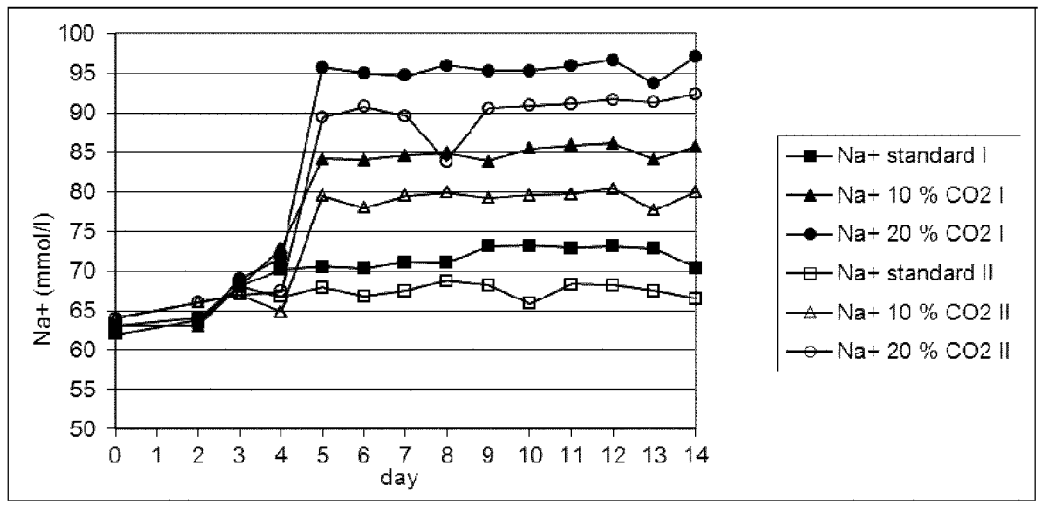
Figure 22:
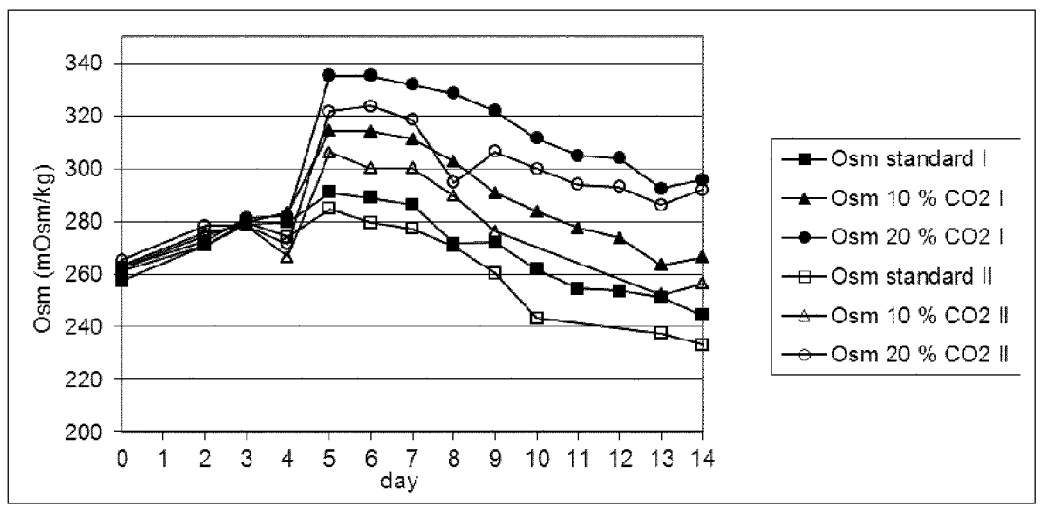
Figure 23:
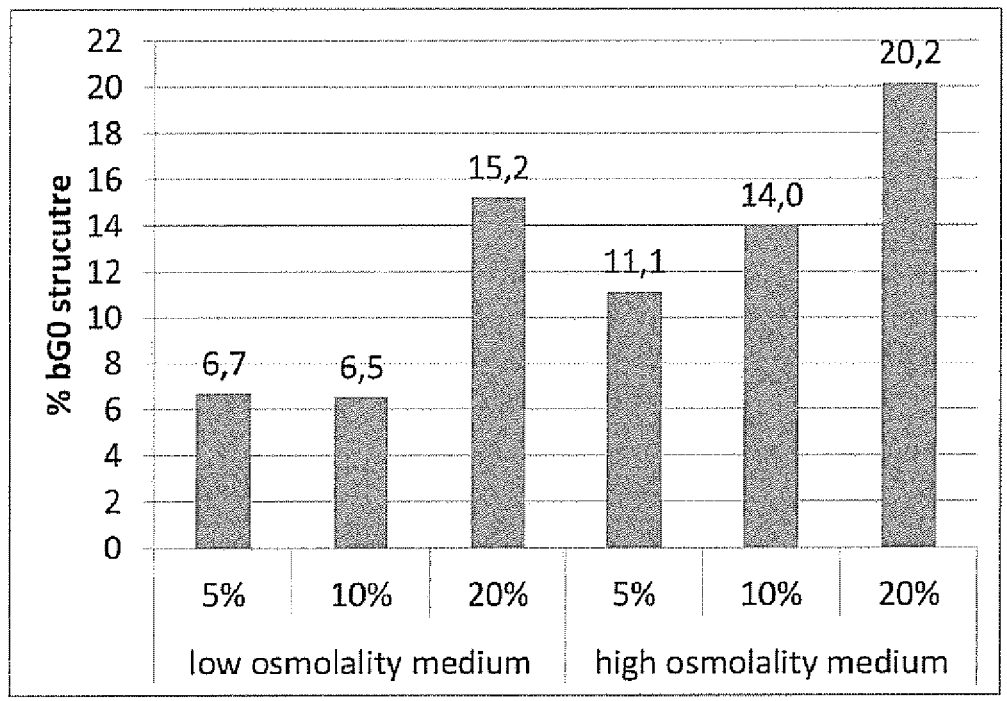

In the accompanying figures, the following disclosure is provided:

FIG. 1: Viable cell density (VCD) and viability.
FIG. 2: Glucose and lactate concentration.
FIG. 3: Glutamine and ammonium concentration: Glutamine and ammonium concentrations had a similar profile in all 9 process runs.
FIG. 4: Product concentration and specific cell productivity: Titre and specific cell productivity dynamics in pilot (PIL) bioprocess runs were slightly lower than in laboratory process runs.
FIG. 5: Off-line $pCO_2$ measurement.
FIG. 6: Off-line pH measurement.
FIG. 7: Viable cell density (VCD) and viability.
FIG. 8: Glucose and lactate concentration.
FIG. 9: Glutamine and ammonium concentration.
FIG. 10: Product concentration and specific cell productivity were similar each in all six bioprocess runs.
FIGS. 11-14 depict the $pCO_2$ profiles in a first (FIG. 11) and second (FIG. 12) bioreactor with regulation of $pCO_2$ to 10%, and the $pCO_2$ profiles in a first (FIG. 13) and second (FIG. 14) bioreactor with regulation of $pCO_2$ to 20%, all thereof gathering on-line measurements.
FIG. 15: Off-line $pCO_2$ measurement.
FIG. 16: Off-line pH measurement.
FIG. 17: The glycan profile of the product in laboratory and PIL processes ran under the same conditions, and without direct $CO_2$ regulation.
FIG. 18: Correlation between $pCO_2$ and non-galactosylated bG0 glycoform, galactosylated glycoform bG1(1-3), and galactosylated glycoform bG1(1-6).
FIG. 19: The glycan profile of the product in $pCO_2$ non-regulated process, at 10% $pCO_2$ and at 20% $pCO_2$: The bG0 structures were increasing, whereas the bG1 structures were decreasing with increased $pCO_2$ process values.
FIG. 20: Correlation between $pCO_2$ and acidic peaks in CEX profiles: Linear decrease of acidic peaks with increased $pCO_2$ levels (see also Table 1).
FIG. 21: Sodium concentrations in the course of $pCO_2$-regulated bioprocesses. Basically, the concentration of $Na^+$ ions is constant over time, although it is increased starting on day 5 following the addition of NaOH to adjust/maintain the pH at about 6.7 or 6.8 upon activation of the $pCO_2$ controller (see below, section "Direct Regulation", subsection 4 i) in lines 14/15 of page 17). Consequently, the higher the $pCO_2$ set-points are, the higher are the $Na^+$ concentrations.
FIG. 22: Osmolalities in the course of $pCO_2$-regulated bioprocesses. Basically, the osmolalities are declining over time, although they exhibit a discontinuity from day 4 to day 5, which is the consequence of the addition of NaOH to adjust/maintain the pH at about 6.7 or 6.8 (see above, the explanation for FIG. 21). Consequently, the higher the $pCO_2$ set-points the higher the osmolalities.
FIG. 23: Influence of a pCO2 shift on the bG0 glycan structure of a fusion glycoprotein in a 13-day fed batch CHO-K1 cell culture process under low and high osmolality conditions (see Example 4).

TABLE 1

The share of acidic peaks (% AP) defined in CEX profile of the product in $pCO_2$ non-regulated process (standard bioprocess), at 10% $pCO_2$, and at 20% $pCO_2$

| Sample | % AP |
| --- | --- |
| Standard I | 16.04 |
| Standard II | 15.17 |
| 10% $CO_2$ I | 14.66 |
| 10% $CO_2$ II | 14.63 |
| 20% $CO_2$ I | 13.39 |
| 20% $CO_2$ II | 13.86 |

In order to investigate the correlation between the N-glycan (glycosylation) profile and the proportion of acidic variants of recombinantly produced polypeptides/proteins and in particular of antibodies on the one hand and the process conditions (parameters) on the other, several fed-batch bioprocesses in laboratory (Lab) and pilot (PIL) process scale were performed with the CHO-SSF3 cell line. The N-glycan structures of primary interest were non-galactosylated bG0 and galactosylated bG1 structures (Table 3). Considering the CEX profiles the present inventors were focusing on acidic variants formed during posttranslational modifications (e.g., by deamidation, isomerisation, glycation, sialylation) of the recombinant polypeptides (and particularly of the antibodies). The main focus of the experiments was on the indirect and direct $pCO_2$ regulation and set-point variation (shift), all as described above, performed in two different production media with the same glucose concentration.

The first experiments focused on indirect $pCO_2$ regulation by pH regulation, where nine fedbatch bioprocesses using the CHO-SSF3 cell line were performed in parallel at 5-, 10-, and 100 liter scale. In all nine bioprocesses the parameters were maintained at the following values:
(a) the initial pH set-point was 7.2, on day 2 after inoculation the pH regulation was turned off, and the natural pH shift was allowed to occur until day 4 after inoculation, when the pH regulation was started again and the pH set-point was shifted to 6.7 and maintained at this value for the rest of the run.
(b) the initial temperature was 37° C. On day 4 after inoculation the temperature set-point was shifted to 33° C. and maintained at this value for the rest of the run.
(c) The partial oxygen pressure ($pO_2$) was 50% during the whole process.

FIG. 5 exhibits indirectly measured (off-line measurement by using Bioprofile 400) $pCO_2$ profiles without $pCO_2$ regulation and shows a clear dependency upon scale (5-liter vs. 10-liter vs. 100-liter batches) and equipment, and even some variability within cultivations at the same scale. Consequently, the correlation between the N-glycan (glycosylation) and CEX profiles on the one hand and the $pCO_2$ profiles were not straightforward. The variability in N-glycan and CEX profiles was very high.

The non-galactosylated bG0 glycoform share in the polypeptide varied from 52.43 to 76.00% and the galactosylated glycoform bG1 share in the same samples varied in the range from 25.60 to 12.56% (FIG. 17). Likewise, in the same samples again, the acidic variants share in the CEX profiles varied from 11.98 to 21.17% (Table 2).

TABLE 2

The share of acidic peaks (% AP) defined in CEX profile of the product in bioprocesses ran under the same conditions (with indirect $CO_2$ regulation)

| Sample | % AP |
| --- | --- |
| PIL61 | 11.98 |
| PIL62 | 12.60 |
| PT01 | 12.91 |
| Lab181 | 17.82 |
| Lab182 | 17.48 |

TABLE 2-continued

The share of acidic peaks (% AP) defined in CEX profile of the product in bioprocesses ran under the same conditions (with indirect $CO_2$ regulation)

| Sample | % AP |
| --- | --- |
| Lab183 | 21.17 |
| Lab184 | 16.60 |
| Lab185 | 15.92 |

In an attempt to further investigate and improve the correlation between the process conditions (parameters) and glycosylation and acidic variants profiles of the recombinant polypeptides, a second set of experiments included six fed-batch bioprocesses, again using the CHO-SSF3 cell line. These six bioprocesses were performed in parallel, but this time direct $pCO_2$ regulation was applied in the production phase of the bioprocess. The $pCO_2$ set-point was varied in the production phase of the bioprocess at the following values: without regulation (standard bioprocess, as control), 10%, and 20%. Two bioprocesses were performed for each $pCO_2$ set-point. The $pCO_2$ controllers were activated on day 4 after inoculation (at the onset of the production phase), immediately after the temperature shift, and maintained at about 10% and 20%, respectively, for the rest of the bioprocesses.

In all six bioprocesses (employing direct $pCO_2$ regulation in the production phase) the parameters pH, temperature, and $pO_2$ were maintained at the following values:
(a) the initial pH set-point was 7.2. On day 2 after inoculation the pH set-point was shifted to 6.8 and maintained at this value until day 4. On day 4, $pCO_2$ regulation was started in 4 bioreactors, regulating $pCO_2$ in 2 bioreactors to 10% and in 2 bioreactors to 20%. The control bioreactors were run without any $pCO_2$ regulation. From day 4, all bioreactors were run without pH regulation.
(b) the initial temperature was 37° C. On day 4 after inoculation the temperature set-point was shifted to 31° C. and maintained at this value for the rest of the run.
(c) the partial oxygen pressure ($pO_2$) was 50%, the aeration total flow 0.15 to 0.40 l/min, stirring at 100 rpm, the pressure in the bioreactor was 1.2 bar, and the culture volume was 10 liters in each case.

Samples for N-glycan analysis were taken from all six bioreactors on the last day (day 14) of the cultivation process. The results show a highly linear correlation between $pCO_2$ and (i) the non-galactosylated bG0 glycoform ($R^2>0.98$), (ii) the galactosylated glycoforms bG1(1-3) ($R^2>0.99$), and (iii) bG1(1-6) ($R^2>0.99$): A higher $pCO_2$ caused higher bG0 and lower bG1 shares in the recombinant polypeptides (see FIG. 18).

The trend for the acidic variants share in the CEX profiles was that an average of 15.61% of the polypeptide produced at non-regulated $CO_2$ was lowered to an average of only 13.63 at 20% $pCO_2$ (Table 1). Additionally, the variability of the results obtained for the glycosylation and CEX profiles was reduced when $pCO_2$ was regulated relative to unregulated $pCO_2$.

Compared to the method of indirectly (via pH) regulating $pCO_2$, the method of direct regulation has proven to be the preferred tool for controlling the bG0 and bG1 structure and acidic variants profile. Additionally, by using direct $pCO_2$ regulation the variability between the bioprocesses was further decreased.

Specifically preferred reaction conditions for the direct and indirect $pCO_2$ regulation are as follows.

Direct Regulation

1. Parameters before inoculation of the bioreactor
   a $pCO_2$ controller is set to ≤10% $pCO_2$, or optionally a pH controller is set to a set-point equal to the initial medium pH value; the $pCO_2$ set-point is selected for each cell line separately, depending on the cell line's capability to grow at the respective $pCO_2$; in other words, it is important to regulate $pCO_2$ such that no detrimental effect on growth of the cells occurs (in case of CHO-SSF3 cells and applied media, a $pCO_2$ of up to 10%/a pH of up to 7.2 is definitely not detrimental to the growth of the cells).

2. Parameters at the time of inoculating the culture medium (day 0)
   i) $pCO_2$ at ≤10% or optionally pH is maintained at or close to the initial medium pH value.
   ii) In case the pH has dropped below the initial medium pH value (e.g., due to the addition of the inoculate), one may or may not adjust the pH to the initial medium pH value (e.g., 7.2) again by adding base (e.g., diluted (2 N) NaOH).

3. Parameters at days 2 and 3 after inoculation
   i) pH is allowed to drop to about 6.7 or 6.8 due to the cells' release of acidic metabolites like lactate and $CO_2$. Optionally, the pH controller is set to a new, more acidic pH.
   ii) pH is maintained at about 6.7 or 6.8 by adding base (e.g., diluted (2 N) NaOH).

4. Parameters on day 4 after inoculation and thereafter
   i) $pCO_2$ controller is set to >10% $pCO_2$. The resulting pH drop is counteracted by NaOH addition (by means of a pH controller) to adjust/maintain the pH at 6.7 or 6.8.
   ii) Cells start to consume acidic metabolites like lactate. Accordingly, pH increases again.
   iii) pH controller is switched off and the pH is maintained at 6.7 or 6.8 by means of a $pCO_2$ controller set to >10% $pCO_2$ by adding $CO_2$ to the medium. pH remains constantly in a slightly acidic range (e.g., around 6.7 or 6.8), $pCO_2$ increases to >10% (according to the second set-point).

Indirect Regulation

1. Parameters before inoculation of the bioreactor
   pH controller is set to the pH of the medium (e.g., 7.2) or slightly below, so that no or only a low amount of $CO_2$ is added to the medium. The pH set-point is optional.

2. Parameters at the time of inoculating the culture medium (day 0)
   After inoculation the pH controller is switched off (i.e., there is no pH regulation any more, neither by $CO_2$ nor by base/NaOH addition), if it had been turned on in 1.

3. Parameters at days 2 and 3 after inoculation
   i) pH is allowed to drop to about 6.7 or 6.8 due to the cells' release of acidic metabolites like lactate and $CO_2$.
   ii) The pH controller is turned on again and set to the new, acidic pH (e.g., 6.7), or slightly below that value so that no or only a low amount of $CO_2$ is added to the medium, in order to maintain the pH at the set-point.

4. Parameters on day 4 after inoculation and thereafter
   i) Cells start to consume acidic metabolites like lactate. Accordingly, pH would increase again, in case of deactivated pH controller.
   ii) pH is maintained at 6.7 or 6.8 by means of a pH controller set to 6.7 or 6.8, adding $CO_2$ to the medium. pH remains constantly in a slightly acidic range (e.g., around 6.7 or 6.8), $pCO_2$ increases to >10% (according to the second set-point).

EXAMPLES

Example 1

Preparation of Inocula for Bioreactor Experiments

The preparation of inocula was initiated with thawing of working cell bank (WCB) vials and inoculation of 250 ml shake flasks containing 50 ml of the pre-production medium. Following sub-cultivation steps in 1-liter (250 ml) and 3-liter (1,000 ml) shake flasks, the culture volume was increased sufficiently to inoculate bioreactors (5 or 10 liters). Additional four sub-cultivations were performed in bioreactors to simulate the number of sub-cultivations predicted for the manufacturing scale process. During pre-production sub-cultivation steps in shake flasks, the conditions in the shaker incubator were set to 37° C., 10% $CO_2$ and a shaking rate of 200 rpm (250-ml and 1-liter shake flasks) and 120 rpm (3-liter shake flasks) at a shaking diameter of 25 mm. The $CO_2$ shaker incubators were not humidified. Pre-production sub-cultivations in the bioreactors were run under the following conditions: 37° C., $pO_2$ of 50%, pH of 7.0, and total flow of gasses ranging from 0.015 to 0.025 vvm (volume per volume per minute; e.g., 0.02 vvm=0.1 liter gas flow/5 liters working (culture) volume in the bioreactor/minute). The initial cell concentration during all pre-production steps was from 2 to $4\times10^5$ viable cells/ml. Duration of the individual sub-cultivation step was 3-5 days.

Production bioprocesses were initiated by transfer of the adequate volume of prepared inocula to 5-liter working volume bioreactors containing the production medium to reach the initial cell concentration of 3 to $5\times10^5$ viable cells/ml and total culture volume of 5 liters.

Example 2

Process Equipment a) Laboratory Scale, Indirect $pCO_2$ Regulation pH shift experiments were performed in 5-liter working volume, stirred tank glass bioreactors with standard mammalian cells cultivation configuration (Sartorius Stedim GmbH Systems). The height/diameter ratio (H/D ratio) of double jacket vessels (the bioreactors) with internal concave bottom was 2:1. The vessels were equipped with two impellers mounted on the stirring shaft: rushtone turbine (diameter D=64 mm) placed at the bottom and marine impeller (D=68 mm) placed at the middle of the stirring shaft. No baffles were used. The following in-line sensors were inserted in the vessel for process control (via control unit):—T sensor (Pt-100),—pH sensor (Mettler Toledo),—$pO_2$ sensor (InPro 6800, Mettler Toledo) and Turbidity probe (Optek inline control). Aeration of cell culture was performed via ring sparger and was regulated by a Gasmix control unit (Sartorius Stedim GmbH Systems) equipped with mass flow controllers (Bronkhorst) for air, $N_2$, $O_2$, and $CO_2$. pH was regulated by $CO_2$/1 M NaOH control loop. For the off-line monitoring of $pCO_2$ the pHOx (Nova, Biomedical) was used.

b) Pilot Process, Direct and Indirect $pCO_2$ Regulation

For the experiments six pilot (steaming in place, cleaning in place) 10-liter stainless steel stirred bioreactors (Applikon) and one 100-liter stainless steel stirred bioreactor (ABN) with standard configuration for mammalian cell culture cultivation were used. The H/D ratio of double jacket vessels with internal concave bottom was 2:1. The vessels were equipped with two impellers mounted on the stirring shaft: rushtone turbine (10-liter: D=100 mm, 100-liter: D=180 mm) placed at the bottom and marine impeller (10-liter: D=100 mm, 100-liter: D=180 mm) placed at the middle of the stirring shaft. No baffles were used in 10-liter bioreactors, and four baffles of standard configuration were used in 100-liter bioreactors. For gassing of the cell culture, a mixing chamber with totaliser and mass flow controllers (Brooks) for air, $N_2$, $O_2$, and $CO_2$ were used. The on-line regulation and monitoring of $pCO_2$ was performed using the submersed on-line InPro 5000 $CO_2$ Sensor (Mettler Toledo AG) and $CO_2$ Transmitter 5100e (Mettler Toledo AG), and for the off-line monitoring the BioProfile 400 (Nova, Biomedical) was used.

For harvest filtration depth filter was used as pre-filter and 0.2 µm filter was used as a final filter.

Example 3

Process Performance

Laboratory Scale, Indirect $pCO_2$ Regulation

Prior to inoculation of the bioreactors, in-line probes (probes inserted in the bioreactor, which enable direct measurement of a specific parameter, e.g., of pH) were calibrated, the vessels (bioreactors) were filled with production medium up to 4.5 liters and process parameters were set as follows: pH at 7.2-natural pH shift at 6.7, temperature at 37° C., partial oxygen pressure ($pO_2$) at 50%, aeration (ring sparger) 100 ml/min and stirring at 140 rpm.

Inoculation of bioreactors was done by transfer of 500 ml of the same inocula, prepared by blending several inocula subcultivated in several shaker flasks, to medium pre-filled bioreactors aiming for starting cell concentrations of $4 \times 10^5$ viable cells/ml. Process parameters were regulated and monitored at the desired set-points via control unit. Process raw data was stored. In respect to cell growth and metabolite consumption, feeding was commenced by introducing the first feed solution, when glucose and glutamine concentrations in the bioreactor dropped to <4 g/l and <4 mM, respectively. The bioreactor was fed up to a glucose and glutamine concentration of 4 g/l and 4 mM, respectively. The second feed solution was added to the bioreactor in a quantity of 0.4% of culture volume on days 7, 10, and 12. The third feed solution was added to the bioreactor in a quantity of 1% of culture volume on the first day after inoculation, and in an amount of 0.2% of the culture volume on days 4, 6, 8, 10, and 12 each. At day 4 after inoculation, a temperature shift from 37 to 33° C. occurred. The pH shift was performed according to experiment plan as follows:

In a natural pH shift experiment the pH controller was switched off at day 0 (the day of inoculation), the initial pH was 7.2, enabling the cells to slowly decrease the pH by lactate production. When the pH dropped to the desired value of 6.7, the controller was switched on again to maintain that desired pH.

Pilot Process, Direct and Indirect $pCO_2$ Regulation

The same procedure as described for the bioprocess at laboratory scale, adopted to volumes of 10 or 100 liters, and a pressure of 1.2 bar was used in pilot scale bioprocesses employing the indirect $pCO_2$ regulation.

For evaluation of the method to directly regulate $pCO_2$, prior to inoculation six bioreactors were filled with production medium. The incubation parameters were set at the following values: pH at 7.2, temperature at 37° C., partial oxygen pressure ($pO_2$) at 50%, gassing (ring sparger) total flow at 150 ml/min, stirring at 100 rpm, and pressure in the bioreactor at 1.2 bar. All six bioreactors were inoculated with the same inocula, prepared by blending several inocula subcultivated in several shaker flasks, to an initial density of 3 to $4 \times 10^5$, preferably $3.5 \times 10^5$ viable cells/ml.

At the process start, the pH was regulated with $CO_2$ in order to maintain the initial pH set-point (7.2). At day 2 after inoculation, the pH started to decrease as consequence of the formation and accumulation of acidic metabolites like lactate. The set-point was changed to 6.8 and the pH regulation with NaOH was started to maintain the pH. At day 4 after inoculation, when the concentration of the viable cells exceeded $3 \times 10^6$ viable cells/ml, the temperature was shifted to 31° C. In parallel, $CO_2$ regulation was started in four bioreactors, regulating the partial $CO_2$ pressure in two bioreactors to 10% and in the other two bioreactors to 20%. Two control bioreactors were run without $CO_2$ regulation.

Beginning day 4 after inoculation, the acidic metabolites such as lactate started to get consumed. Consequently the pH started to increase. The pH controllers were switched off in all bioreactors in order to prevent the $CO_2$ addition for decreasing the pH value to the set-point in bioreactors ran without $CO_2$ regulation, while in bioreactors ran with $CO_2$ regulation $CO_2$ addition was regulated by $pCO_2$ controllers set to $pCO_2$ of 10% or 20%.

All other incubation parameters remained constant from days 4 to 14 after inoculation (at day 14 after inoculation the bioprocess was terminated). To maintain $pO_2$ at 50%, the total gas flow was increased according to the oxygen demand to 0.21 to 0.39 l/min.

To maintain the optimal conditions for the cell culture, two feeds were needed to be added. The first feeding solution was added on daily basis beginning day 4 after inoculation, when the glutamine concentration dropped to below 4 mM. The amount of feed was calculated to get 4 mM as a final glutamine concentration. The second feeding solution was added on days 7, 10, and 12 after inoculation.

Sampling of Bioreactors and Harvests and Processing of Samples for Analysis

Bioreactors were sampled daily (3×1 ml) for cell count, measuring the concentration of metabolites (glutamine, glucose, lactate, $NH_4^+$), off-line pH, the gas content ($CO_2$, $O_2$), and pH. All measurements were performed immediately after sampling in untreated samples. Samples for determining the concentration of the product (recombinantly produced polypeptide), i.e., the titre, were taken on days 3, 7, 10, 12, and 14 after inoculation, sterile filtrated, and measured via ALC (affinity liquid chromatography).

Final Harvest Analyses

Harvests were collected at the end of a 14-day fed-batch (2×50 ml), centrifuged (Eppendorf Centrifuge 5810R; 3220 rcf (relative centrifugal force), 10 mM), sterile filtered through a PES membrane filter (Sartorius Sartopore 2, 0.2+0.1 μm) and stored at −85° C. For the purpose of analytical characterisation, the exemplary recombinant protein (a monoclonal antibody directed to tumour necrosis factor, TNF) was purified from harvests with a single affinity chromatography purification step using MabSelect SuRe affinity columns. Purification was done either by using the AKTA chromatography system available from GE Healthcare with a 1 mL HiTrap column (GE Healthcare). In detail, the columns were first equilibrated with 50 mM sodium phosphate, pH 7.0. Then up to 4 mg (RoboColumns) or 20 mg (HiTrap columns) of the antibody were loaded onto the columns, followed by a washing step with 50 mM sodium phosphate, pH 7.0. The antibody was then eluted with 50 mM sodium acetate, pH 3.5, and collected in sample tubes pre-filled with neutralisation buffer (10 mM TRIS base). Columns were then regenerated with 1 M acetic acid and cleaned with 0.1 M sodium hydroxide. Columns were stored in 20% ethanol.

Analytical Methods for Process Performance and Product Quality Determination

Cell concentrations were monitored with a Vi-Cell XR analyser (Beckman-Coulter), basic metabolites were determined with a Bioprofile 400 analyser (Nova Biomedical), the gas content ($CO_2$, $O_2$) and pH were measured by pHOx (pilot scale measurements performed with Bioprofile 400) analyser (Nova Biomedical). Product concentration (titre) in the cell culture was determined via ALC.

Asialo N-glycan mapping was performed according to SOP 83.567, Edition 1.0 (Sandoz). The glycosylation profiles were determined according to 2-AB-labelled NPC (2-Aminobenzamide-labelled normal phase chromatography).

This SOP describes a quantitative analysis method for N-glycans from the Fc part of from monoclonal antibodies and consists of following subchapters:
- the release of N-glycans from monoclonal antibodies (MAb),
- the separation of N-glycans from the de-glycosylated MAb,
- the labeling from N-glycans with 2-aminobenzamide (2-AB),
- the cleanup of 2-AB labeled N-glycans,
- the profiling of 2-AB labeled glycans by normal phase chromatography.

SOP=Standard Operating Procedure

Structures identified in Gmap chromatograms are listed in Table 3.

TABLE 3

Identification of Glycan Mapping Chromatograms Structures

| | PEAK NO. | | | |
|---|---|---|---|---|
| | 1 | 2 | 3 | 4 |
| N-Glycan | bG0(−N) | bG0(−F) | bG0 | Man5 |

TABLE 3-continued

Identification of Glycan Mapping Chromatograms Structures

| PEAK NO. | | | |
|---|---|---|---|
| 5 | 6 | 7 | 8 |
| N-Glycan bG1(-N) | bG1(1-6) | bG1(1-3) | Man6 |

| PEAK NO. | | | |
|---|---|---|---|
| 7 | 8 | 7 | 8 |
| N-Glycan bG2 | Man7 | bG2S1* | Man8 |

Symbols for monosaccharides
F: Fucose △
G: Galactose ○
M: Mannose ●
N: N-acetyl glucosamine □
$S_A$: N-acetyl neuraminic acid ◆
$S_G$: N-glycolyl neuraminic acid ◈

In addition to the structures listed in Table 3, four consistent peaks eluting prior to bG0(-N) were designated as unknown group and were later identified as M3(-F), M3, bG0(-N—F). An unknown peak eluting prior to bG2 was designated as unk1. The percentage of incidental peak areas was presented as N.A.

A structure, first designated as bG1S1 according to retention times obtained from glycan profiles of other mAb, was later identified as high-Man structure, most likely Man8.

The CEX profiles were determined in desalinated harvest protein A eluates by cation exchange HPLC.

Results

Summary of Output Parameters of Lab and PIL Bioprocesses for Evaluation of the Indirect $pCO_2$ Regulation Method:

The cell concentration increased exponentially up to day 4 after inoculation when the temperature shift was performed. The cell concentration remained stable from day 5 after inoculation to the end of the process and ranged from 5.5 to $7.5 \times 10^6$ viable cells/ml, depending on the process run. Viability was around 90% in PIL and about 95% in Lab processes at the beginning of the process, after day 4 after inoculation it was slightly increased in all processes until day 11 after inoculation, when it began to drop. Viability at the end of the process ranged from 82 to 95% (see FIG. 1).

The glucose concentration dropped up to day 4 after inoculation when the first feeding solution was first added to the bioreactors. The glucose concentration profile was similar over the culturing time in all process runs during the whole process. In the laboratory process runs the accumulation of lactate (lower trend chart on FIG. 2) observed on day 3 and after day 7 after inoculation (FIG. 2) was higher than in PIL bioprocess runs.

The $pCO_2$ profiles are shown in FIG. 5, where the off-line measurements are summarised. The values in 5-liter Lab bioprocesses are higher, despite the same pH regulation strategy as in PIL bioprocesses. The main reason for the discrepancy after day 5 and particularly after day 6 after inoculation is probably the 0.2 bar overpressure in PIL bioreactors entailing higher $CO_2$ solubility and lower amounts of $CO_2$ needed to maintain the same pH value (i.e., 6.7) in PIL bioreactors. Additionally, the reason for the discrepancy in $CO_2$ profiles between PIL and lab bioprocesses may be, to some extent, especially in a phase of low lactate concentrations and consequently high $pCO_2$ (after day 6 after inoculation, see FIG. 2), due to different sampling procedures, analytical equipment, and $CO_2$ evaporation in PIL processes samples.

The pH values were changing during the processes as shown in FIG. 6. The discrepancy in measurements between pilot and laboratory processes are due to the $CO_2$ evaporation in pilot processes in case of off-line $CO_2$ measurements. The on-line pH values after the pH shift were in a range of 6.7±0.05 in all bioprocesses.

Summary of Output Parameters of PIL Bioprocesses for Evaluation of the Direct $pCO_2$ Regulation Method:

The cell concentration increased exponentially from day 1 to day 4 after inoculation (the temperature shift was done at day 4 after inoculation) and remained more or less stable from day 5 or 6 after inoculation to the end of the process. It ranged from 4 to $6 \times 10^6$ viable cells/ml, depending on the process run (FIG. 7). Viability was around 95% from the beginning of the process to day 12 after inoculation, when it began to drop. At the end of the process viability was about 75 to 90% (FIG. 7).

The glucose concentration dropped from day 0 to day 4 after inoculation (the first feeding solution was first added to the bioreactors at day 4 after inoculation). The glucose concentration profile was similar over incubation time in all process runs during the whole process (FIG. 8). Similar profiles in all process runs were observed also for the lactate concentrations (FIG. 8).

Likewise, the glutamine concentration has the same profile in all six process runs, as shown in FIG. 9. Quite conversely, the ammonium concentration varied depending on the $CO_2$ concentration in the bioreactors. The ammonium concentration remained high (around 6 mM) when $pCO_2$ was regulated to 20%. The lower $pCO_2$ was regulated, the higher the drop of the ammonium concentration after day 5 after inoculation was (FIG. 9).

During incubation of the cells, the pH was regulated only to reach the target pH range (6.8 to 7.2) until day 4 after inoculation, when the pH regulation was switched off. The pH then changed during the processes (FIG. 16).

Results of PIL Bioprocesses for Evaluation of the Direct $pCO_2$ Regulation Method:

The results showed a highly linear correlation between $pCO_2$ and (a) non-galactosylated bG0 ($R^2 > 0.98$), (b) galactosylated bG1(1-3) ($R^2 > 0.99$), and (c) bG1(1-6) ($R^2 > 0.99$) glycoforms, where increasing $pCO_2$ caused the bG0 levels to likewise increase and the bG1 levels to decrease in the recombinant polypeptides/proteins (see FIG. 18).

CONCLUSIONS

Although it brought about results that were to the inventors' satisfaction, the method to indirectly (by pH regulation) regulate $pCO_2$ does not seem to be the optimum choice for bioprocess performance control. This was mainly manifested in differences in lactate and dissolved $CO_2$ concentration ($pCO_2$) profiles between Lab and the corresponding PIL processes, leading to a comparably high variability in product quality (glycan, CEX profiles), i.e., depending on which process (Lab, PIL) was performed, the profiles were distinct. On the other hand, the experiments performed and described herein demonstrate that direct $pCO_2$ regulation is a preferred and more suitable tool to control the ratio of bG0 and bG1 structures, and to lower the amount of acidic variants in recombinantly produced polypeptides/proteins and particularly antibodies, and to lower variability between distinct bioprocesses. Despite the non-optimal results of indirect $pCO_2$ regulation the skilled artisan would still consider the indirect $pCO_2$ regulation because the implementation/installation of the technical equipment (e.g., of a $pCO_2$ controller, etc.) needed for the direct $pCO_2$ regulation in already established manufacturing or development facilities can be time-, labour-, and money-consuming (for example a re-approval of the production facility by the regulatory authorities might become necessary, because of the newly introduced $pCO_2$ operating parameter etc.).

Example 4

Effect of $CO_2$ on Protein Glycosylation

This experiment was performed to confirm the effect of $CO_2$ control during the cell culture process on protein glycosylation under conditions other than those described in the preceding sections. These different conditions include: cell line, expressed recombinant product and its glycosylation pattern, additional high osmolality medium variant, $CO_2$ shifting timepoint, and growth system.

Experimental Setup:

A CHO-K1 cell line expressing a glycosylated fusion protein was used. Two medium variants were designed: a low osmolality (250 mOsm/kg) and a high osmolality variant (340 mOsm/kg). For each osmolality, the cells were grown in three 500 ml shake flasks (Corning, USA) containing 125 ml cell culture. Incubation was performed in $CO_2$ shaker incubators (Kühner) using a 25 mm shaking diameter. The initial incubation conditions were kept at 36.5° C., at a 200 rpm shaking rate and at a 5% $CO_2$ atmosphere. On day 4, the temperature was shifted to 33° C. On day 6, one shake flask each was left at 5% $CO_2$, whereas the second shake flask was transferred into a $CO_2$ incubator set at 10% $CO_2$ and the third one was transferred into a $CO_2$ incubator set at 20% $CO_2$ (direct $pCO_2$ regulation was used throughout the experiment). Culturing of the cells was continued until day 13. Afterwards, the cell cultures were centrifuged, the supernatants containing the recombinant protein were sterile filtered, and the recombinant protein was purified using affinity chromatography and hydrophobic chromatography before performing glycan analysis.

Results:

As depicted in FIG. 23, the portion of the recombinant protein having bG0 glycan structure was increased by increasing the $CO_2$-values (from day 6 to 13), although it was similar in low osmolality media at 5 and 10% $CO_2$ (6.7% vs. 6.5%). However, a significant increase was observed when shifting to 20% $CO_2$ (15.2%). When working with high osmolality media, a trend of increasing portions of bG0-structure with increasing $CO_2$-values (from day 6 to 13) was observed, even at lower $CO_2$-values: 11.1, 14.0 and 20.2% corresponding to 5%, 10%, and 20% $CO_2$ (from day 6 to 13), respectively. Also, higher bG0 values were observed in the higher osmolality media.

REFERENCES

Butler M. 2006. Optimisation of the cellular metabolism of glycosylation for recombinant proteins produced by mammalian cell systems. *Cytotechnology.* 50:57-76.

Lipscomb M L, Palomares L A, Hernandez V, Ramirez O T, Kompala D S. 2005. Effect of production method and gene amplification on the glycosylation pattern of a secreted reporter protein in CHO cells. *Biotechnol Prog.* 21:40-49.

Takuma S, Hirashima C, Piret J M. 2007. Dependence on glucose limitation of the $pCO_2$ influences on CHO cell growth, metabolism and IgG production. *Biotechnol Bioeng.* 97:1479-1488.

Trummer E, Fauland K, Seidinger S, Schriebl K, Lattenmayer C, Kunert R, Vorauer-Uhl K, Weik R, Borth N, Katinger H, et al. 2006. Process parameter shifting: Part II. Biphasic cultivation-A tool for enhancing the volumetric productivity of batch processes using Epo-Fc expressing CHO cells. *Biotechnol Bioeng.* 94:1045-1052.

Zanghi J A, Schmelzer A E, Mendoza T P, Knop R H, Miller W M. 1999. Bicarbonate concentration and osmolality are key determinants in the inhibition of CHO cell polysialylation under elevated pCO(2) or pH. *Biotechnol Bioeng.* 65:182-191.

The invention claimed is:

1. A method of controlling quality and quantity of post-translational modification of a recombinantly produced polypeptide/protein (glycoprotein), wherein the posttranslational modification affects the glycosylation profile and/or the acidic variants profile, as manifested in CEX profiles, wherein the glycosylation profiles are selected from bG0 structures and bG1 structures, and wherein the polypeptide/protein (glycoprotein) production is in eukaryotic host cells, the method comprising the following steps:
   a) cultivating the eukaryotic cells in a suitable medium under conditions which allow the expression of the polypeptide/protein, wherein the content of the dissolved $CO_2$ ($pCO_2$) in the medium is at a first value during the initial growth phase of the eukaryotic cells, allowing the eukaryotic cells to grow, and
   b) increasing the content of the dissolved $CO_2$ ($pCO_2$) in the existing medium of step a) during the production phase of the eukaryotic cells to a second $pCO_2$ value, wherein the amount of bG0 structures is increased and the amount of bG1 structures is decreased, relative to the amounts obtained by a method with no pCO2 regulation.

2. The method claim 1, wherein the acidic variants are selected from deamidated, isomerised, glycated, and sialylated variants of the recombinantly produced polypeptide/protein.

3. The method of claim 1, wherein the acidic variants profile is defined by a reduced amount of acidic variants in the recombinantly produced polypeptide/protein, relative to the amount obtained by a method with no $pCO_2$ regulation.

4. The method of claim 1, wherein the first $pCO_2$ value is set at ≤10% and the second $pCO_2$ value is set at >10%.

5. The method of claim 4, wherein the first $pCO_2$ value is set in the range of 2% to 8%, and the second $pCO_2$ value is set in the range of 11% to 40%.

6. The method of claim 1, wherein the cell is an insect or mammalian cell.

7. The method of claim 6, wherein the mammalian cell is a CHO cell or a hybridoma.

8. The method of claim 1, wherein the glycosylated polypeptide is an antibody, or a fragment or derivative thereof.

9. The method of claim 8, wherein said antibody, or fragment or derivative thereof, is selected from:
   a) a hybridoma-derived antibody, or a fragment or derivative thereof,
   b) a chimerised antibody, or a fragment or derivative thereof,
   c) a humanised antibody, or a fragment or derivative thereof, and/or
   d) a human antibody, or a fragment or derivative thereof.

10. The method of claim 8, wherein said antibody, or fragment or derivative thereof, is an IgG, an IgG fragment, or IgG derivative.

11. The method of claim 1, wherein the second $pCO_2$ value is reached by a stepwise or gradually decrease or increase in $CO_2$ content.

12. The method of claim 1, wherein the content of dissolved $CO_2$ ($pCO_2$) in the medium is directly regulated by means of a control system with a $pCO_2$-controller equipped with a mass flow controller.

13. The method of claim 1, wherein the content of dissolved $CO_2$ ($pCO_2$) in the medium is indirectly regulated by regulating the pH.

14. The method of claim 5, wherein the first $pCO_2$ value is in the range of 3.5% to 6.5%, or 4.5% to 5.5%.

15. The method of claim 5, wherein the second $pCO_2$ value is set in the range of 12% to 35%, 15% to 25%, or 18.5% to 22.5%.

16. The method of claim 10, wherein said IgG, IgG fragment, or IgG derivative is an anti-TNFα-, anti-VEGF-, anti-HER2-, anti-CD20-, or anti-EGFR-antibody, or a fragment or derivative thereof.

17. The method of claim 1, wherein the bG0 structures are bG0(-N), bG0(-F), and/or bG0.

18. The method of claim 1, wherein the bG1 structures are bG1(-N), bG1(1-6), and/or bG1(1-3).

* * * * *